US012265078B2

(12) United States Patent
Li et al.

(10) Patent No.: US 12,265,078 B2
(45) Date of Patent: Apr. 1, 2025

(54) MODELING NEUROLOGICAL DISORDERS AND ATAXIAS WITH CARDIAC DYSFUNCTION USING BIOENGINEERED HEART TISSUES

(71) Applicant: NOVOHEART INTERNATIONAL LIMITED, Kowloon (HK)

(72) Inventors: Ronald A. Li, Hong Kong (CN); Kevin D. Costa, New York, NY (US)

(73) Assignee: NOVOHEART INTERNATIONAL LIMITED, Kowloon (HK)

( * ) Notice: Subject to any disclaimer, the term of this patent is extended or adjusted under 35 U.S.C. 154(b) by 1007 days.

(21) Appl. No.: 17/041,912

(22) PCT Filed: Mar. 28, 2019

(86) PCT No.: PCT/IB2019/000498
§ 371 (c)(1),
(2) Date: Sep. 25, 2020

(87) PCT Pub. No.: WO2019/186283
PCT Pub. Date: Oct. 3, 2019

(65) Prior Publication Data
US 2021/0132043 A1 May 6, 2021

Related U.S. Application Data

(60) Provisional application No. 62/649,468, filed on Mar. 28, 2018.

(51) Int. Cl.
*C12M 3/00* (2006.01)
*C12N 5/077* (2010.01)
(Continued)

(52) U.S. Cl.
CPC ....... *G01N 33/5044* (2013.01); *C12N 5/0657* (2013.01); *G01N 33/5082* (2013.01); *G01N 2500/10* (2013.01)

(58) Field of Classification Search
CPC .............................. C12M 35/02; C12N 5/0657
See application file for complete search history.

(56) References Cited

U.S. PATENT DOCUMENTS

2013/0137132 A1* 5/2013 Dekker .................. C12Q 1/025
216/17
2014/0349332 A1 11/2014 Yasuda et al.
(Continued)

FOREIGN PATENT DOCUMENTS

WO 2010/127280 A1 11/2010
WO 2014/047387 A2 3/2014
(Continued)

OTHER PUBLICATIONS

Wilson et al., Dynamic microRNA expression programs during cardiac differentiation of human embryonic stem cells: role for miR-499, Circ. Cardiovasc Genet., 3:426-435 (2010).
(Continued)

*Primary Examiner* — Nathan A Bowers
(74) *Attorney, Agent, or Firm* — MARSHALL, GERSTEIN & BORUN LLP

(57) ABSTRACT

A system for screening compounds for therapeutic cardiac effects in the cells, tissues and organoids (1) of patients having diseases such as neurological diseases or disorders with significant cardiac comorbidities. The system comprises a medical device apparatus that can be suitable for a single-tier screen for cardio-active compounds that comprises a human ventricular cardiac anisotropic sheet (hvCAS) and human ventricular cardiac tissue strip (hvCTS), a two-tier system further comprising human ventricular cardiac organoid chamber (hvCOC) (20), or a three-tier system still further comprising a medical device comprising multiple organoids (20), which include tissues or organoids (1) of the same or different type (e.g., heart, liver, pancreas, kidney). Another aspect of the disclosure is the
(Continued)

methods suitable for use with the systems, comprising screens for identifying compounds having cardiac effects on cells, tissues or organoids (1) of patients having a non-cardiac disease exhibiting a cardiac effect, such as neurological diseases. The methods are further useful in assessing the toxicity of compounds to various cells, tissues or organoids (1) of such patients.

25 Claims, 16 Drawing Sheets

(51) Int. Cl.
    *G01N 5/00* (2006.01)
    *G01N 33/50* (2006.01)

(56) References Cited

U.S. PATENT DOCUMENTS

| | | | |
|---|---|---|---|
| 2015/0313704 A1* | 11/2015 | Thavandiran | C12N 5/0657 623/23.72 |
| 2016/0003806 A1* | 1/2016 | Parker | G01N 33/5061 506/10 |
| 2017/0107469 A1 | 4/2017 | Costa et al. | |

FOREIGN PATENT DOCUMENTS

| | | |
|---|---|---|
| WO | 2015/081226 A1 | 6/2015 |
| WO | 2016/036532 A1 | 3/2016 |
| WO | 2016/069142 A2 | 5/2016 |
| WO | 2017/059171 A1 | 4/2017 |
| WO | 2018/029535 A1 | 2/2018 |

OTHER PUBLICATIONS

Zhang et al., Consensus Comparative Analysis of Human Embryonic Stem Cell-Derived Cardiomyocytes, PLoS One, 10:e0125442 (2015).
Zhuo Z., Laser interference testing technology and applications, Machinery Industry Press, pp. 52-53, Oct. 1998.
Al-Mahdawi et al., Gaa repeat expansion mutation mouse models of Friedreich ataxia exhibit oxidative stress leading to progressive neuronal and cardiac pathology, Genomics, 88:580-590 (2006).
Casazza et al., The varying evolution of Friedreich's ataxia cardiomyopathy, Am. J. Cardiol., 77:895-898 (1996).
Cashman et al., Construction of defined human engineered cardiac tissues to study mechanisms of cardiac cell therapy, J. Vis. Exp., 109:e53447 (2016).
Chan et al., Label-free separation of human embryonic stem cells and their cardiac derivatives using Raman spectroscopy, Anal. Cham., 81:1324-1331 (2009).
Chen et al., Phospholamban as a Crucial Determinant of the Inotropic Response of Human Pluripotent Stem Cell-Derived Ventricular Cardiomyocytes and Engineered 3-Dimensional Tissue Constructs, Circ. Arrthyhm. Electrophysiol., 8:193-201 (2015).
Chen et al., Shrink-film configurable multiscale wrinkles for functional alignment of human embryonic stem cells and their cardiac derivatives, Adv. Mater., 23:5785-5791 (2011).
Chow et al., Epigenetic regulation of the electrophysiological phenotype of human embryonic stem cell-derived ventricular cardiomyocytes: insights for driven maturation and hypertrophic growth, Stem Cells Dev., 22:2678-2690 (2013).
Dixon et al., The role of iron and reactive oxygen species in cell death, Nat. Chem. Biol., 10:9-17 (2014).
Durr et al., Clinical and genetic abnormalities in patients with Friedreich's ataxia, N. Engl. J. Med., 335:1169-1175 (1996).
Edenharter et al., Overexpression of *Drosophila frataxin* triggers cell death in an iron-dependent manner, J. Neurogenet., 31:189-202 (2017).
European Application No. 19774875.9, European Search Report and Opinion, mailed Dec. 14, 2021.
Filla et al., The relationship between trinucleotide (gaa) repeat length and clinical features in Friedreich ataxia, Am. J. Hum. Genet., 59:554-560 (1996).
Fu et al., Distinct roles of microRNA-1 and -499 in ventlicular specification and functional maturation of human embryonic stem cell-derived cardiomyocytes, PLoS One, 6:e27417 (2011).
Fu et al., Na+/Ca2+ exchanger is a determinant of excitation-contraction coupling in human embryonic stem cell-derived ventricular cardiomyocytes, Stem Cells Dev., 19:773-782 (2010).
Goffart et al., Regulation of mitochondrial proliferation in the heart: Power-plant failure contributes to cardiac failure in hypertrophy, Cardiovasc Res., 64(2):198-207 (2004).
Hick et al., Neurons and cardiomyocytes derived from induced pluripotent stem cells as a model for mitochondrial defects in Friedreich's ataxia, Dis. Model Mech., 6:608-621 (2013).
International Application No. PCT/IB19/00498, International Preliminary Report on Patentability, mailed Oct. 8, 2020.
International Application No. PCT/IB19/00498, International Search Report and Written Opinion, mailed Nov. 13, 2019.
Isnard et al., Correlation between left ventricular hypertrophy and gaa trinucleotide repeat length in Friedreich's ataxia, Circulation, 95:2247-2249 (1997).
Karakikes et al., Correction of human phospholamban RI4del mutation associated with cardiomyopathy using targeted nucleases and combination therapy, Nat. Commun., 6:6955 (2015).
Karakikes et al., Small Molecule-Mediated Directed Differentiation of Human Embryonic Stem Cells Toward Ventricular Cardiomyocytes, Stem Cells Transl. Med., 3:18-31 (2014).
Keung et al., Non-cell autonomous cues for enhanced functionality of human embryonic stem cell-derived cardiomyocytes via maturation of sarcolemmal and mitochondrial KATP channels, Sci. Rep., 6:34154 (2016).
Kipps et al., The longitudinal course of cardiomyopathy in Friedreich's ataxia during childhood, Pediatr Cardiol., 30:306-310 (2009).
Lee et al., Efficient attenuation of Friedreich's ataxia (FRDA) cardiomyopathy by modulation of iron homeostasis-human induced pluripotent stem cell (hiPSC) as a drug screening platform for FRDA, Int. J. Cardiol., 203:964-971 (2016).
Lee et al., Modeling of Friedreich ataxia-related iron overloading cardiomyopathy using patient-specific-induced pluripotent stem cells, Pflugers Arch., 466:1831-1844 (2014).
Li et al., Bioengineering an electro-mechanically functional miniature ventricular heart chamber from human pluripotent stem cells, Biomaterials, 163:116-127 (2018).
Li et al., Mechanistic basis of excitation-contraction coupling in human pluripotent stem cell-derived ventricular cardiomyocytes revealed by Ca2+ spark characteristics: Direct evidence of functional Ca2+-induced Ca2+ release, Heart Rhythm, 11:133-140 (2014).
Lieu et al., Absence of Transverse Tubules Contributes to Non-Uniform Ca2+ Wavefronts in Mouse and Human Embryonic Stem Cell-Derived Cardiomyocytes, Stem Cells Dev., 18:1493-1500 (2009).
Lieu et al., Mechanism-Based Facilitated Maturation of Human Pluripotent Stem Cell-Derived Cardiomyocytes, Circ. Arrhythm. Electrophysiol., 6:191-201 (2013).
Liu et al., Facilitated maturation of Ca2+ handling properties of human embryonic stem cell-derived cardiomyocytes by calsequestrin expression, Am. J. Physiol. Cell Physiol., 297:C152-159 (2009).
Liu et al., Functional sarcoplasmic reticulum for calcium handling of human embryonic stem cell-derived cardiomyocytes: insights for driven maturation, Stem Cells., 12:3038-44 (2007).
Lopaschuk et al., Energy metabolic phenotype of the cardiomyocyte during development, differentiation, and postnatal maturation, J. Cardiovasc Pharmacol., 56:130-140 (2010).
Luna et al., Multiscale Biomimetic Topography for the Alignment of Neonatal and Embryonic Stem Cell-Derived Heart Cells, Tissue Eng Part C Methods, 17:579-588 (2011).
Lynch et al., Management and therapy for cardiomyopathy in Friedreich's ataxia, Expert Rev Cardiovasc Ther., 10:767-777 (2012).
Martelli et al., Dysregulation of cellular iron metabolism in Friedreich ataxia: From primary iron-sulfur cluster deficit to mitochondrial iron accumulation, Front. Pharmacol., 5:130 (2014).

(56) References Cited

OTHER PUBLICATIONS

Miranda et al., Frataxin knockin mouse, FEES Lett., 512:291-297 (2002).

Payne et al., Cardiomyopathy of Friedreich's ataxia: Use of mouse models to understand human disease and guide therapeutic development, Pediatr Cardiol., 32:366-378 (2011).

Poon et al., Proteomic Analysis of Human Pluripotent Stem Cell-Derived, Fetal, and Adult Ventricular Cardiomyocytes Reveals Pathways Crucial for Cardiac Metabolism and Maturation, Circ. Cardiovasc Genet., 8:427-436 (2015).

Poon et al., Transcriptome-Guided Functional Analyses Reveal Novel Biological Properties and Regulatory Hierarchy of Human Embryonic Stem Cell-Derived Ventricular Cardiomyocytes Crucial for Maturation, PLoS One, 8:e77784 (2013).

Puccio et al., Mouse models for Friedreich ataxia exhibit cardiomyopathy, sensory nerve defect and fe-s enzyme deficiency followed by intramitochondrial iron deposits, Nat. Genet., 27:181-186 (2001).

Rajagopalan et al., Analysis of the factors influencing the cardiac phenotype in Friedreich's ataxia, Mov. Disord., 25:846-852 (2010).

Ramirez et al., Pathology of intercalated discs in Friedreich cardiomyopathy, J. Am. Coll. Cardiol., 66:1739-1740 (2015).

Shum et al., A micropatterned human pluripotent stem cell-based ventricular cardiac anisotropic sheet for visualizing drug-induced arrhythmogenicity, Adv. Mater., 29(1):1602448 (2017).

Tandon, N., et al., Electrical stimulation systems for cardiac tissue engineering, Nature Protocols, 4(2):155-173 (2009).

Tsou et al., Mortality in Friedreich ataxia, J. Neural. Sci., 307:46-49 (2011).

Turnbull et al., Advancing functional engineered cardiac tissues toward a preclinical model of human myocardium, FASEB J., 28:644-654 (2014).

Wang et al., Effect of engineered anisotropy on the susceptibility of human pluripotent stem cell-derived ventricular cardiomyocytes to arrhythmias, Biomaterials, 34:8878-8886 (2013).

Wang et al., Electrophysiological properties of pluripotent human and mouse embryonic stem cells, Stem Cells, 23(10):1526-34 (2005).

Weidemann et al., The cardiomyopathy in Friedreich's ataxia—new biomarker for staging cardiac involvement, Int. J. Cardiol., 194:50-57 (2015).

Weng et al., A Simple, Cost-Effective but Highly Efficient System for Deriving Ventricular Cardiomyocytes from Human Pluripotent Stem Cells, Stem Cells Dev., 23:1704-1716 (2014).

\* cited by examiner

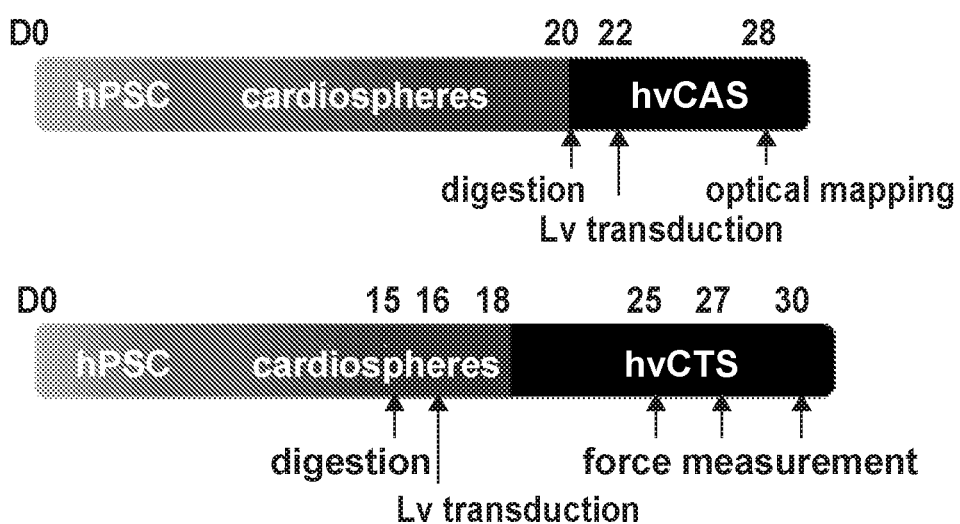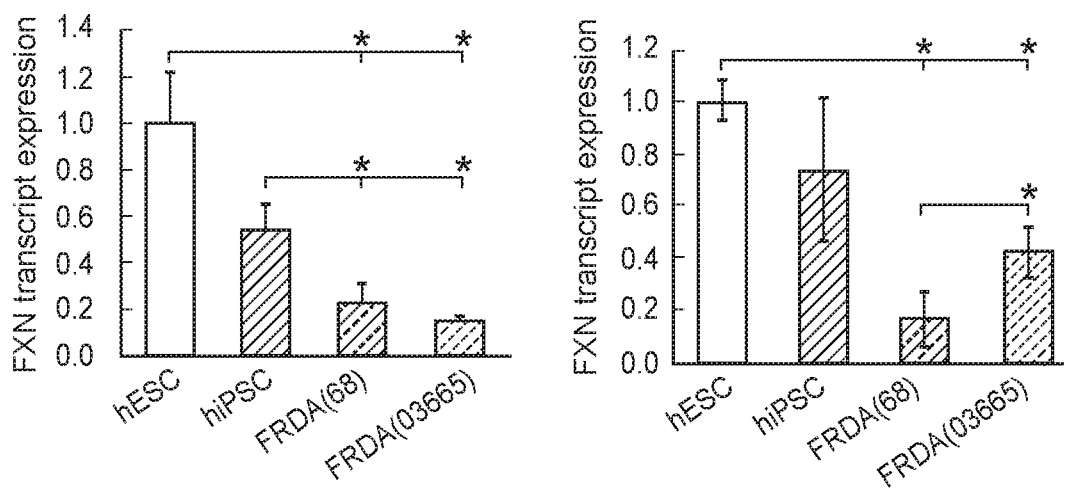
Figure 1

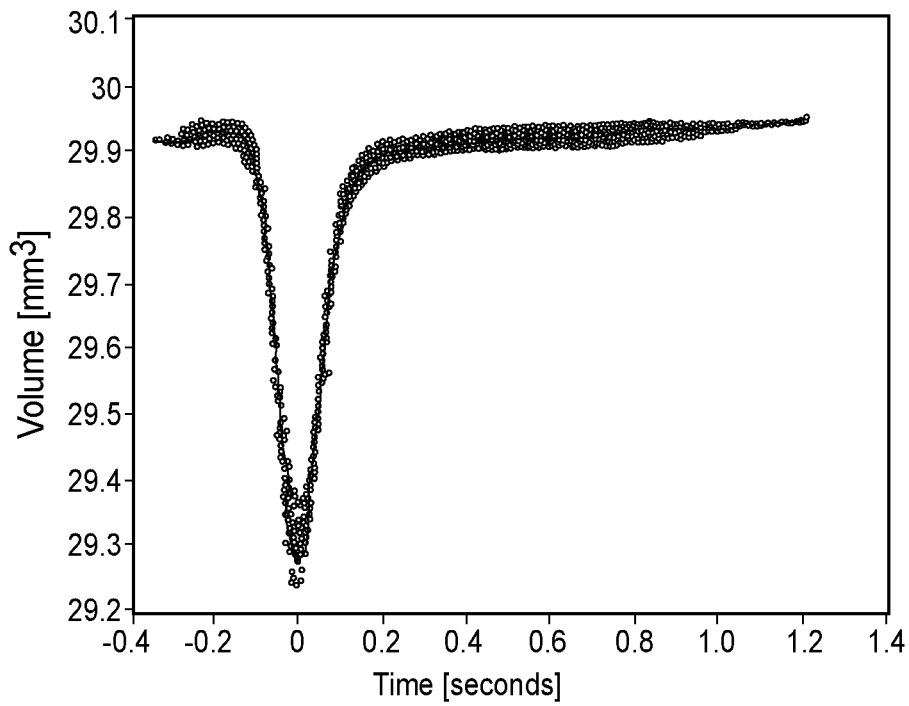
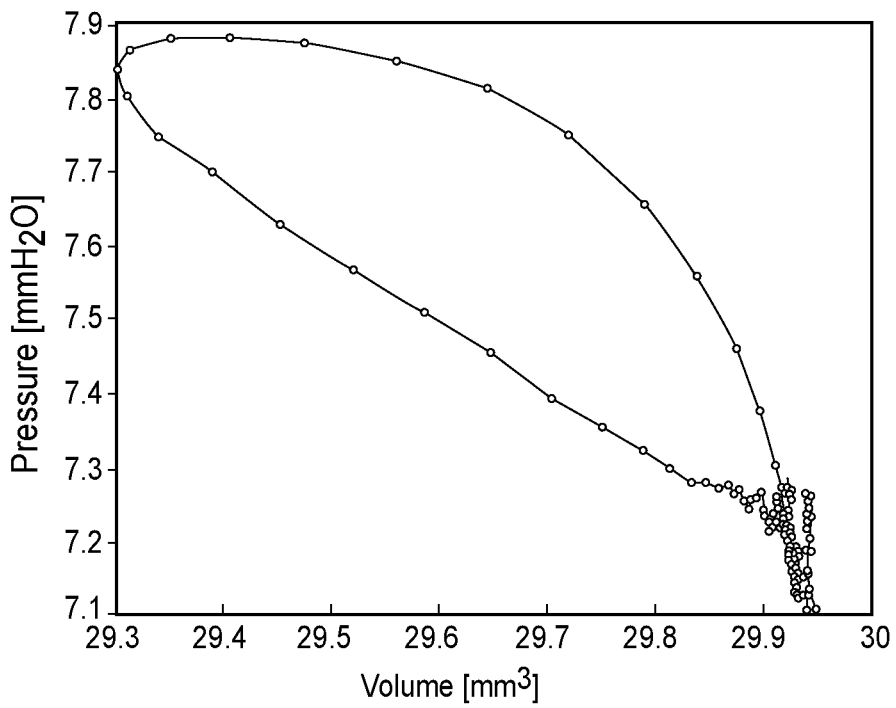
Figure 13

MODELING NEUROLOGICAL DISORDERS AND ATAXIAS WITH CARDIAC DYSFUNCTION USING BIOENGINEERED HEART TISSUES

CROSS-REFERENCE TO RELATED APPLICATION

This application is a U.S. National Phase of PCT/IB2019/000498, filed Mar. 28, 2019, which claims the priority benefit of provisional U.S. Patent Application No. 62/649,468, filed Mar. 28, 2018, incorporated herein by reference.

FIELD

The disclosure relates generally to the fields of medical health and cardiac physiology and, more specifically, to the field of in vitro models and screens for cardiac effects in cells from diseased patients.

BACKGROUND

Friedreich's ataxia (FRDA) is a hereditary neurodegenerative disease caused by a mutation in the first intron of the frataxin (FXN) gene on chromosome 9, whereby tri-nucleotide guanine-adenine-adenine (GAA) sequences that normally repeat up to 40 times in healthy individuals reoccur hundreds to more than a thousand times. Even though fully functional wild-type FXN proteins are produced in FRDA patients, the intronic mutation yields a significant reduction in the amount of FXN expression resulting in only 5 to 30% of residual protein compared to that in non-carriers. FXN, a mitochondrial protein involved in the biosynthesis of iron-sulfur clusters, is crucial for ATP production.

Due to its reliance on mitochondria for high energy consumption, the heart is a major site of pathology in patients. FRDA-induced cardiac symptoms are first detected as abnormal electrocardiogram (EKG) and can progress to compensatory hypertrophic cardiomyopathy, dilated cardiomyopathy, and then to cardiomyocyte (CM) death and fibrosis, which consequently lead to heart failure and arrhythmias. Indeed, the leading cause of death in FRDA patients has been attributed to cardiac problems. However, the correlation between the severity of FRDA-induced cardiac symptoms and FXN expression has not been established.

Considering the high level of amino acid identity among the FXN genes across species, murine models have been generated to study FRDA pathology. One murine model is achieved through a conditional ablation of the Fxn gene that results in a complete knockout of Fxn in targeted organs[11]. Although this particular model presents expected FRDA phenotypes, such as cardiomyopathy and mitochondrial defects, its genotype does not reflect that of FRDA in patients. Another mouse model simulating the human genotype has been generated through transgenic expression of the human FXN gene with expanded GAA repeats in combination with knockout of the murine Fxn gene; however, the severity of the diseased phenotypes does not match that observed in FRDA patients[14, 15]. Therefore, an in vitro model using human CMs appear to be a more suitable and relevant model for studying the cardiac pathogenesis of FRDA. However, patient biopsies are limited in availability, and inadequate for recapitulating functional phenotypes of the disease such as contractile dysfunction.

With advances in reprogramming, human induced pluripotent stem cells (hiPSCs) can be derived from FRDA patients and differentiated into CMs to study the disease progression in a human in vitro model. To date, however, there are no reports or disclosures examining or suggesting the examination of the contractile or electrophysiological properties of such CMs in a multicellular, cardiomimetic model.

Much effort has been expended to advance our understanding of the human cardiovascular system and human cardiac care, but a need continues to exist in the art for biological models that can rapidly and accurately reveal cardiac effects in cells from patients having diseases that are conventionally understood as being non-cardiac in nature.

SUMMARY

To improve and extend the lives of patients with neurological diseases or disorders that have deleterious cardiac comorbidities, therapeutics targeting the cardiac symptoms (which are often the leading cause of mortality) would be most valuable. In order to test candidate therapeutics that might target, and treat, such cardiac effects, an effective in vitro platform that can fully recapitulate the disease phenotype, i.e., suitable disease model(s), needs to be created. Animal models have been used heavily for the past several decades, but have proven to be poorly predictive of outcomes in patients because the human heart differs significantly from non-human hearts. Unfortunately, patient heart biopsies are in very limited supply, and such isolated tissues are not viable for long outside the body. Recent development of pluripotent stem cell technology has allowed the mass production of human heart cells (cardiomyocytes), which offer an attractive platform for disease modeling. Cultured cardiomyocytes have limited capabilities in disease modeling, however, because single-cell properties are difficult to extrapolate into tissue-level phenotypes, and traditional monolayer cultures do not recapitulate the anisotropic three-dimensional structure and function of heart tissue. Engineered human heart tissues can solve this problem as they can be assessed functionally, and are tailored in their design to allow readouts which can be much more easily related to clinical symptoms. An integrated suite of engineered cardiac tissue assays could thus offer advantages over any one system for comprehensively evaluating therapeutics for cardiac diseases with neuropathological foundations. To illustrate the benefits of the disclosure in assessing candidate therapeutics and identifying treatments for the cardiac effects associated with neurological diseases, the description below focuses on what can be done to address the cardiac deficiencies associated with Friedreich's ataxia. The description is an exemplary description of the benefits of the disclosure, which can readily be applied to model other neurological diseases having cardiac effects by those skilled in the art.

Disclosed herein are studies showing, for the first time, the effects of reduced FXN level on cardiac electrophysiology and contractile properties with various engineered tissue constructs fabricated from FXN-deficient human ventricular CMs (hvCMs) derived from human embryonic stem cells (hESCs) or hiPSCs (collectively termed human pluripotent stem cells, or hPSCs), in which FXN levels were either reduced by short hairpin RNA (shRNA)-mediated knockdown of FXN (in hESCs and healthy hiPSCs) or were naturally low by virtue of a mutation in the FXN gene in the donor patient (in FRDA hiPSCs). The studies disclosed herein took advantage of tissue platforms providing a human ventricular cardiac anisotropic sheet (hvCAS)[19-22] for modeling cardiac electrophysiology and arrhythmias, a human ventricular cardiac tissue strip (hvCTS)[23-24] for modeling cardiac force generation and contractility defects, and/or a human ventricular cardiac organoid chamber (hvCOC) designed to simulate a more physiological condition with electrically and mechanically coupled CMs. These tissue platforms are superior models for studying the FRDA pathogenesis, by enabling readouts such as conduction velocity, magnitude of force generation, and cardiac output that are otherwise not possible in single-cell or many other engineered tissue models.

Generally, the present disclosure provides a system, and associated methods, to facilitate drug discovery/screening using engineered hvCASs, hvCTSs and hvCOCs that model neurological diseases having at least one deleterious cardiac effect. These engineered constructs can be assembled using (a) healthy hPSC-derived CMs (or hPSC-CMs) engineered to reproduce the effect of the disease-causing mutation in patient CMs, for example by lentiviral shRNA-mediated knockdown of one or more specific genes, or (b) intrinsically diseased hiPSC-derived CMs (or hiPSC-CMs) derived from patients carrying one or more disease-causing mutations. The biofidelity of the model is validated against clinically observed symptoms (e.g., alterations in electrocardiographic patterns, contractile dysfunction) of the patients, and compared with relevant healthy controls (for example, healthy hPSC-CMs transduced with a non-targeting shRNA lentiviral control, or hiPSC-CMs derived from healthy subjects) to ensure the specificity of the model. The validated model is useful for screening of treatments for beneficial or toxic effects on the cardiac tissue(s). These engineered constructs can be employed to assess electrophysiological and contractile effects of candidate treatments on the heart, both in terms of toxicity and efficacy, with the objective of identifying treatments that can ameliorate, rescue or abolish disease symptoms, without causing deleterious side-effects. For example, for FRDA, which shows both electrophysiological and contractile symptoms, efficacy and safety screening can be performed concurrently using both electrophysiological (hvCAS) and contractile (hvCTS/hvCOC) models. Treatments, either singular or combinatorial, that can induce improvement in both types of symptoms identify promising candidate therapeutics.

The hvCAS disease model is a bio-hybrid material in the form of (1) human ventricular cardiomyocytes (hvCMs), and (2) a microfabricated substrate providing an attachment point for the growth and ordered development of the hvCMs, as fundamental building blocks that have been strategically aligned by design. In use, the hvCMs form a monolayer of cells (termed the human ventricular cardiac anisotropic sheet or hvCAS) plated on microfabricated substrates, which provide environments conducive to the development of the anisotropic properties characteristic of human cardiac cells in vivo. The disease-modeling hvCMs can be either (a) healthy hPSC-derived CMs (or hPSC-CMs) engineered to reproduce the effect of the disease-causing mutation in patient CMs, for example by lentiviral shRNA-mediated knockdown of one or more specific genes, or (b) intrinsically diseased hiPSC-derived CMs (or hiPSC-CMs) derived from patients carrying one or more disease-causing mutations. In some embodiments, the microfabricated substrate comprises grooves oriented along a single axis of the substrate. In some embodiments, the grooves have similar dimensions. In some embodiments, the grooves have a width of 1-30 μm, including embodiments wherein the grooves have a width of 5-15 μm, such as wherein the grooves have a width of 15 μm. In some embodiments, the depth of the grooves is about 5 μm. In some embodiments, the spacing between grooves is about 5 μm.

One aspect of the disclosure provides a method of modeling the electrophysiological phenotypes of a disease comprising: (a) fabricating an hvCAS with disease-modeling CMs either engineered from healthy hPSCs or derived from patient hiPSCs; (b) stimulating the anisotropic layer of cells at one or more points; (c) detecting an electrical signal propagation in the anisotropic layer of cells; and (d) assessing the electrophysiological properties of the hvCAS. In various embodiments, the electrophysiological property of the hvCAS that is assessed is action potential duration, transverse conduction velocity, longitudinal conduction velocity, anisotropic ratio, automaticity (presence of spontaneous action potentials), maximum capture frequency, maximum upstroke velocity, maximum decay velocity, rise time, conduction pattern, occurrence of arrhythmic events in the form of spiral electrical propagation waves, and/or any other physiological parameter of cardiomyocytes that can be monitored using an anisotropic sheet of cardiomyocytes. In some embodiments, the anisotropic layer of cells comprises ventricular cardiomyocytes derived from a human. Embodiments of this aspect of the disclosure exist wherein the microfabricated substrate is polystyrene. In some embodiments, the cardiac anisotropic layer of cells is stimulated at one point, such as wherein the stimulation is 5-30 volts with a pulse duration of 5-30 milliseconds. In an exemplary embodiment, the stimulation is 10 volts with a pulse duration of 10 milliseconds. In some embodiments of this aspect of the disclosure, the electrical stimulation induces a spiral electrical propagation wave in the hvCAS disease model, mimicking arrhythmia in the clinical symptoms of the disease. In some embodiments the hvCAS disease model exhibits altered electrophysiological parameters such as action potential duration and conduction velocity.

More specifically, an aspect of the disclosure is drawn to a system for screening a compound for an electrophysiological effect on cardiomyocytes of a diseased organism or engineered cardiomyocytes comprising: (1) human ventricular cardiomyocytes (hvCMs), and (2) a microfabricated substrate providing an attachment point for the growth and ordered development of the hvCMs, as fundamental building blocks that have been strategically aligned by design. In use, the hvCMs form a monolayer of cells (termed the human ventricular cardiac anisotropic sheet or hvCAS) plated on microfabricated substrates, which provide environments conducive to the development of the anisotropic properties characteristic of human cardiac cells in vivo. The method is amenable to screens of candidate compounds to identify compounds having an electrophysiological effect on cardiomyocytes of diseased organisms and to screens of known therapeutics useful in treatments to identify those therapeutics having an electrophysiological effect on cardiomyocytes. The disease-modeling hvCMs can be either (a) healthy hPSC-derived CMs (or hPSC-CMs) engineered to reproduce the effect of the disease-causing mutation in patient CMs, for example by lentiviral shRNA-mediated knockdown of one or more specific genes, or (b) intrinsically diseased hiPSC-derived CMs (or hiPSC-CMs) derived from patients carrying one or more disease-causing mutations. In some embodiments, the grooves have similar dimensions. In some embodiments, the grooves have a width of 1-30 μm, including embodiments wherein the grooves have a width of 5-15 μm, such as wherein the grooves have a width of 15 μm. In some embodiments, the depth of the grooves is about 5 μm. In some embodiments, the spacing between grooves is about 5 μm. One aspect of the disclosure provides a method of screening the electrophysiological effects of a treatment comprising: (a) contacting an hvCAS disease model with a treatment; (b) stimulating the hvCAS disease model at one or more points; (c) detecting an electrical signal propagation in the hvCAS disease model; and (d) determining whether the compound exhibits efficacy (for example by abrogating arrhythmia as indicated by absence or reduction of spiral electrical propagation waves) or toxicity (for example by inducing or exacerbating spiral electrical propagation waves). Embodiments of this aspect of the disclosure exist wherein the microfabricated substrate is polystyrene. In some embodiments, the hvCAS is stimulated at one point, such as wherein the stimulation is 5-30 volts with a pulse duration of 5-30 milliseconds. In an exemplary embodiment, the stimulation is 10 volts with a pulse duration of 10 milliseconds. In some embodiments of this aspect of the disclosure, the electrical stimulation induces a spiral electrical propagation wave in the hvCAS disease model, mimicking arrhythmia induced by the treatment. In some embodiments the treatment induces changes in electrophysiological parameters such as action potential duration and conduction velocity in the hvCAS disease model.

The hvCTS disease model or the hvCAS disease model can be paired with the hvCOC disease model in a two-tiered screen, with a first-tier screen using an hvCTS to assess contractile effects on the heart or hvCAS to assess one or more physiological parameters of cardiomyocytes, followed by a second-tier screen on the higher order biological structure of the hvCOC system, to confirm the findings of the first-tier screen and to reveal any organoid- or organ-level effects not apparent from the cells used in the first-tier screen. The disclosure further provides for the possibility of a third screen, which may be viewed as a third-tier screen, optimally combined with the first- and second-tier screens. In the third-tier screen, multiple organoids are screened using a multi-organoid system. The third tier screen yields data that is even more reliable than the data obtained from two-tiered screening. In addition, the multi-organoid format allows for multiple organoids of the same type, e.g., cardiac organoids, to be used in the screen and/or for different interconnected organoids to be used in the third-tier screen at the same time, using the versatile multi-organoid system disclosed herein. (As used herein, "organoid" typically refers to an organ-like biomaterial, but the term can also refer to an engineered tissue, which can be considered an organ-like biomaterial. The meaning of the term used herein will be apparent from the context of its usage.) In some embodiments, the human ventricular cardiac tissues comprise hPSC-derived ventricular cardiomyocytes (vCMs). The single-cell properties of such cells, such as electrophysiology (action potential, $Ca^{2+}$ handling), transcriptome, proteome, and the like, have been extensively characterized by our team[30-48]. As disclosed herein, various cells, e.g., human ventricular cardiomyocytes, may be used in developing the organoids used in the second-tier hvCOC system and in developing the organoids used in the third-tier multi-organoid system.

The multiorganoid system used in the second and third tiers of the multi-tiered systems and methods of the disclosure is a platform that simultaneously characterizes multiple in vitro tissue-engineered tissues or organoids, including a mirror arrangement together with a single detection device. Equipped with a fluidic exchange network, organoids are interconnected in this platform to model a "mini-human" system that simulates systemic drug responses in human patients that is useful in replacing animal testing as the default in vivo model. The semi-automated platform includes multiple features to aid in investigating functional response to delivered drugs, such as environmental control (e.g., temperature and $CO_2$), high-speed camera, synchronized pressure-volume recordings, interconnected fluidic exchange system, drug perfusion, intra-organoid pressure control, mechanical stimulation, and electrical stimulation. These features are designed to improve culture handling, permit examination of long-term drug exposure of tissues or organoids, and allow simultaneous multi-tissue and/or multi-organ drug response. Current in vitro therapeutic screening typically assesses only the acute response of single tissues or organoids, which makes scaling up challenging and costly. By using a single camera with a mirror arrangement for multi-organoid imaging, this system is more scalable than currently available designs.

To develop next-generation in vitro human models, the bioreactor platform includes a modular organoid cartridge system and a fluid exchange network that enables a flexible systems biology approach. "Plug-and-play" organoid cartridges expedite the process of imaging various tissue and/or organoid combinations of interest within the bioreactor. In addition, the circulation and exchange of media between tissues or organoids recapitulates the human circulatory system. Signaling factors and metabolites can be freely exchanged between tissues or organoids and can affect the drug response of one or more tissues or organoids. Such "body-in-a-jar" technology facilitates drug discovery and precision, or personalized, medicine efforts, and is superior to organ-on-a-chip technologies that often fail to fully recapitulate organ function owing to the lack of three-dimensional organization.

New molecular entities are characterized using clinically relevant endpoints (e.g., ejection fraction in heart tissue, permeability in lung tissue) and then classified using automated computer algorithms (e.g., machine learning) trained to detect patterns of bioactivity and toxicity. The multi-organoid imaging platform disclosed herein increases throughput and is useful for higher content screening. By improving throughput, the system becomes more accessible to preclinical pharmaceutical screening. The platform is also used to probe basic biology in tissue-engineered human constructs derived from patients with neurological diseases or disorders.

In addition to the tier one hvCTS system and method, the disclosure provides a versatile bioreactor platform for developing engineered organoid tissues that more closely mimic the in vivo structure and function of the corresponding human organ. With a combination of a high-speed camera and pressure transducers, the disclosure provides a method to combine spatiotemporal movement of shifting tissues or organoids (e.g., contracting heart organoid) with pressure recordings to measure pressure-volume relationships. In addition, the disclosure provides a sophisticated system for fluidic exchange within the bioreactor platform through the coordinated use of fluidic pumps, three-way valves and fluid tanks, as opposed to some systems using simple hydrostatic pressure systems. The fluidic exchange system also provides for connection of any number of organoids within the bioreactor. The fluidic exchange system of the disclosure provides the additional functions of controlling media delivery for feeding, aspirating media, the mixing of bioactive components (e.g., therapeutics), and the injection of bioactives on an acute schedule (e.g., a bolus) or a chronic schedule (e.g., perfusion). Bioactive components may include, but are not limited to, drug compounds, viral vectors, conditioned media, progenitor cells, and extracellular vesicles. The fluidic exchange system also provides for cleaning, rinsing or washout of fluidic lines. In addition, the disclosure provides for mechanical stimulation of developing tissues or organoids by applying a method for mechanical stretching to tissues or organoids with cavities. By applying mechanical stretching, the disclosure provides a means for manipulating tissues or organoids, given that mechanical stretch can act as a mechanotransduction signal. In contrast to electrical pacing of human cardiac organoids via field stimulation, the disclosure provides for point stimulation of such organoids, resulting in a more precise and refined stimulation of organoid tissues. With point stimulation, electrical conduction measurements within a tissue or organoid (e.g., heart) can be accomplished, for example by using optical mapping techniques. Further, the application of machine learning principles in the analysis of tissue or organoid behavior according to the disclosure is expected to improve evaluation of therapeutic response outcomes by comprehensively analyzing and understanding high-dimensional parameter spaces. All of the benefits are provided in an integrated package by the disclosure, representing a significant advance in the field of therapeutic screening, including new methods, i.e., experimental assays, that are expected to lead to improved prevention, treatment and/or amelioration of cardiac symptoms associated with various neurological diseases, disorders and conditions.

More specifically, one aspect of the disclosure is drawn to a system for screening a compound for a cardiac effect, e.g., a contractile effect, on cardiomyocytes of a diseased organism or engineered cardiomyocytes comprising: (a) a screening apparatus comprising: (i) a biocompatible gel comprising a plurality of cardiomyocytes of a diseased organism or a plurality of engineered cardiomyocytes; (ii) a biocompatible support apparatus for suspending the biocompatible gel, wherein the biocompatible gel and biocompatible support apparatus form a cardiac tissue strip comprising cardiomyocytes of a diseased organism or engineered cardiomyocytes; (iii) a detection device for detecting movement of the biocompatible gel; and (iv) an electrical power source for applying an electrical pacing stimulus to the biocompatible gel. The compound can be a therapeutic known to be useful in a cardiac treatment because of its contractile effect on cardiomyocytes, or the compound can be a candidate therapeutic. In some embodiments, the system for screening a compound further comprises: (a) a second-stage screening apparatus comprising: (i) at least one organoid module comprising at least one organoid cartridge, wherein the organoid cartridge comprises a media inlet, a media outlet, and at least one wall compatible with an external detection device, wherein each organoid cartridge comprises a cardiomyocyte of a diseased organism or an engineered cardiomyocyte, and wherein at least one organoid cartridge comprises cardiomyocytes of a diseased organism or engineered cardiomyocytes; and (ii) a detection device for observing the monitored biological development of the cardiomyocytes of a diseased organism or the engineered cardiomyocytes in each organoid cartridge. In some embodiments, the second-stage screening apparatus disclosed herein further comprises a mirror arrangement for simultaneous monitoring of any biological development of the cardiomyocytes of a diseased organism or engineered cardiomyocytes in each organoid cartridge.

Another aspect of the disclosure is a system for screening a compound for a cardiac effect on cardiomyocytes of a diseased organism or engineered cardiomyocytes comprising: (a) a screening device comprising: (i) an anisotropic layer of cardiac cells on a microfabricated substrate; (ii) an electrical power source for stimulating the anisotropic layer of cells at one or more points; and (iii) a detection device for detecting an electrical signal propagation in the anisotropic layer of cells. In some embodiments, the microfabricated substrate comprises grooves oriented along a single axis of the substrate. In some embodiments, the grooves have a width of 1-30 µm, the depth of the grooves is about 5 µm, the spacing between grooves is about 5 µm, or a combination thereof. In some embodiments, the electrical power source is at least one electrode, such as a single electrode or an array of electrodes, or at least one electrified portion of the substrate. The partially or completely electrified substrate is capable of establishing an electric field that may be uniform or may exhibit a gradient. In some embodiments, the system for screening a compound for a cardiac effect that comprises a screening device further comprises (a) a second-stage screening apparatus comprising: (i) at least one organoid module comprising at least one organoid cartridge, wherein the organoid cartridge comprises a media inlet, a media outlet, and at least one wall compatible with an external detection device, wherein each organoid cartridge comprises a cardiomyocyte of a diseased organism or an engineered cardiomyocyte, and wherein at least one organoid cartridge comprises cardiomyocytes of a diseased organism or engineered cardiomyocytes; and (ii) a detection device for observing the monitored biological development of the cardiomyocytes of a diseased organism or engineered cardiomyocytes in each organoid cartridge.

In some embodiments of the systems according to the disclosure, the cardiomyocytes are human cardiomyocytes, such as human ventricular cardiomyocytes, e.g., wherein the cardiomyocytes are present at a concentration of at least $10^6$ cells/ml.

In some embodiments of the system, the cardiomyocytes are engineered cardiomyocytes or are produced from hiPSCs which are derived from a patient having a neurological disease that includes, but is not limited to, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers). In some embodiments, the cardiomyocytes are engineered to have low FXN expression or are derived, e.g., from hiPSCs, from a patient with Friedreich's ataxia (FRDA).

In some embodiments of the system, the cardiomyocytes are genotypically normal and derived from healthy hPSCs, including established hESCs or hiPSCs from healthy volunteers, and engineered to recapitulate the mutant disease phenotype typical of a neurological disease including, but not limited to, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers), for example wherein the cardiomyocytes are engineered to express reduced levels of frataxin (FXN) protein as typically observed in FRDA patients.

In some embodiments, the biocompatible gel comprises matrigel, such as a gel wherein the matrigel is present at a concentration of at least 0.5 mg/ml. In some embodiments, the biocompatible gel further comprises collagen, e.g., wherein the collagen is type I human collagen. In some embodiments, the collagen is present at a concentration of at least 1 mg/ml.

The support apparatus for the biocompatible gel may be at least two vertical support members. In some embodiments, the vertical support members are made of polydimethylsiloxane. In particular embodiments, there are two vertical support members that are each approximately circular in cross-section with a diameter of about 0.5 mm. In some embodiments, the cardiac tissue strip is about 26.5 mm in length by about 16 mm in width by about 6 mm in height.

The system disclosed herein contemplates embodiments wherein the detection device is a high-speed camera. In some embodiments, the mirror arrangement of the second-stage screening apparatus comprises at least one pyramidal mirror. Some embodiments of the screening system comprise a second-stage screening apparatus that further comprises an electrode in adjustable relation to the tissue or organoid in at least one organoid cartridge. In some embodiments, the second-stage screening apparatus further comprises a temperature control element, a light source, a module access port, or any combination thereof. In some embodiments, the system comprising the second-stage screening apparatus further comprises a data processor in electronic communication with the detection device, a temperature control element, a light source, a module access port or any combination thereof. In some embodiments, the detection device is a digital camera, at least one pressure transducer, or a combination of a digital camera and at least one pressure transducer.

Further contemplated by the disclosure is a system further comprising a monitor. In some embodiments, the system comprising the second-stage screening apparatus comprises a plurality of organoid modules. Some embodiments of this system further comprise an interconnected fluid exchange network, wherein the network comprises a plurality of fluid lines, a plurality of valves, at least one pump, and at least one fluid tank. Some embodiments further comprise a port for introduction of a compound. In some embodiments, the interconnected fluid exchange network comprises fluid communication between at least two organoid cartridges. In some embodiments, the fluid is media. Some embodiments further comprise a gas pressure controller, such as embodiments wherein the gas pressure controller controls the concentration of at least one of $O_2$ and $CO_2$ in at least one module or in one or more organoid cartridges. Some embodiments further comprise a drug perfusion apparatus for delivery of a compound to the cell, tissue, or organoid. Some embodiments further comprise a media mixer.

Yet another aspect of the disclosure is a method of screening for a compound having a cardiac effect comprising: (a) pacing a cardiac tissue strip as disclosed herein with an electrical stimulus at a pacing frequency of 0.5 Hz, 1.0 Hz, 1.5 Hz or 2.0 Hz in the presence or absence of a candidate cardiac compound; (b) detecting any movement of the paced cardiac tissue strip in the presence or absence of the candidate cardiac compound; (c) comparing the movement of the paced cardiac tissue strip in the presence of the candidate cardiac compound to the movement of the paced cardiac tissue strip in the absence of the candidate cardiac compound; and (d) determining that the candidate cardiac compound is a cardiac compound when the movement of the paced cardiac tissue strip differs in the presence of the compound compared to the movement of the paced cardiac tissue strip in the absence of the compound. In some embodiments of the method, the pacing frequency is 1.0 Hz. In some embodiments, the compound is a drug, a viral vector, conditioned media, extracellular vesicles, additional cells, or any combination thereof. In some embodiments, the method further comprises an assay to measure the toxicity of the compound.

In some embodiments of the method, the cardiomyocytes are engineered cardiomyocytes or are cardiomyocytes produced from hiPSCs derived from a patient having a neurological disease including, but not limited to, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers). In some embodiments, the cardiomyocytes are engineered to have low FXN expression or are derived from a patient with Friedreich's ataxia (FRDA). In some embodiments, the engineered cardiomyocytes are genotypically normal and derived from healthy hPSCs, including established embryonic stem cell lines or hiPSCs from healthy volunteers, and engineered to recapitulate the mutant disease phenotype typical of a neurological disease including, but not limited to, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers), for example wherein the cardiomyocytes are engineered to express reduced levels of frataxin (FXN) protein as typically observed in FRDA patients. In some embodiments of the method of screening for a compound that involves monitoring the movement of a paced cardiac tissue strip, the method further comprises: (a) contacting an anisotropic layer of cardiac cells on a microfabricated substrate with a compound; (b) using an electrical power source to stimulate the anisotropic layer of cells at one or more points; (c) detecting an electrical signal propagation in the anisotropic layer of cells; and (d) determining whether the cardiac cells exhibit a cardiac effect in the presence compared to the absence of the compound.

Still another aspect of the disclosure is a tissue monitoring system comprising (a) at least one organoid module comprising a plurality of organoid cartridges, wherein each organoid cartridge comprises a media inlet, a media outlet, and at least one wall compatible with an external detection device, wherein a plurality of the organoid cartridges each comprise a cardiomyocyte of a diseased organism or an engineered cardiomyocyte; (b) a mirror arrangement for simultaneous monitoring of any biological development of the cardiomyocyte of a diseased organism or the engineered cardiomyocyte in each of at least two organoid cartridges; and (c) a detection device for observing the monitored biological development of the cardiomyocyte of a diseased organism or the engineered cardiomyocyte in each of at least two organoid cartridges. In some embodiments, the cardiomyocyte is an engineered cardiomyocyte or a cardiomyocyte derived from a patient having a neurological disease including, but not limited to, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers). In some embodiments, the cardiomyocyte is engineered to have low FXN expression or is derived from a patient with Friedreich's ataxia (FRDA). In some embodiments of the system, the cardiomyocytes are engineered cardiomyocytes that are genotypically normal and derived from healthy hPSCs, including established embryonic stem cell lines or hiPSCs from healthy volunteers, and engineered to recapitulate the mutant disease phenotype typical of a neurological disease including, but not limited to, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers), for example wherein the cardiomyocytes are engineered to express reduced levels of frataxin (FXN) protein as typically observed in FRDA patients.

In some embodiments, the mirror arrangement comprises at least one pyramidal mirror. Some embodiments further comprise an electrode in adjustable relation to the cell, tissue, or organoid in at least one organoid cartridge. In some embodiments, the detection device is a recording device. Some embodiments further comprise a temperature control element, a light source, a module access port, or any combination thereof. Some embodiments further comprise a data processor in electronic communication with the detection device, a temperature control element, a light source, a module access port or any combination thereof. In some embodiments, the recording device is a digital camera, at least one pressure transducer, or a combination of a digital camera and at least one pressure transducer. Some embodiments further comprise a tissue comprising at least one human cell. Some embodiments of the system further comprise a monitor.

In some embodiments, the system comprises a plurality of organoid modules. Some embodiments further comprise an interconnected fluid exchange network, wherein the network comprises a plurality of fluid lines, a plurality of valves, at least one pump, and at least one fluid tank. Some embodiments further comprise a port for introduction of a compound. In some embodiments, the fluid is media. Some embodiments further comprise a gas pressure controller, such as embodiments wherein the gas pressure controller controls the concentration of at least one of 02 and $CO_2$ in at least one module or in one or more organoid cartridges. Some embodiments further comprise a plurality of module access ports. Some embodiments further comprise a drug perfusion apparatus for delivery of a therapeutic to the cell, tissue, or organoid.

Other features and advantages of the disclosed subject matter will be apparent from the following detailed description and figures, and from the claims.

BRIEF DESCRIPTION OF THE DRAWING

FIG. 1. In vitro modeling of FRDA by engineered cardiac tissue constructs of FXN-deficient hPSCs. A) Experimental timeline for generating cardiac tissue models, human ventricular cardiac anisotropic sheet (hvCAS) and human ventricular cardiac tissue strip (hvCTS), for electrophysiological and contractile assessment, respectively. B) FXN transcript and protein expression of hESCs (n=9), hiPSCs (n=9), and FRDA-hiPSC lines 68 (n=10) and 03665 (n=3), normalized to GAPDH expression. Data are shown as mean±SEM. * indicates statistical significance with p<0.05.

FIG. 13. MATLAB analysis to generate average P-V loops from an acquisition. A) Calculation of mean volumetric contraction curve of a tissue. Each volumetric contraction of a beat is plotted as a scatter plot with the time of maximum contraction set to t=0 seconds. Mean curve is denoted as a solid red line. B) Line graph of mean P-V loop summarizing multiple contractions. Red circles denote values at sampled time points.

DETAILED DESCRIPTION

Figure 2:
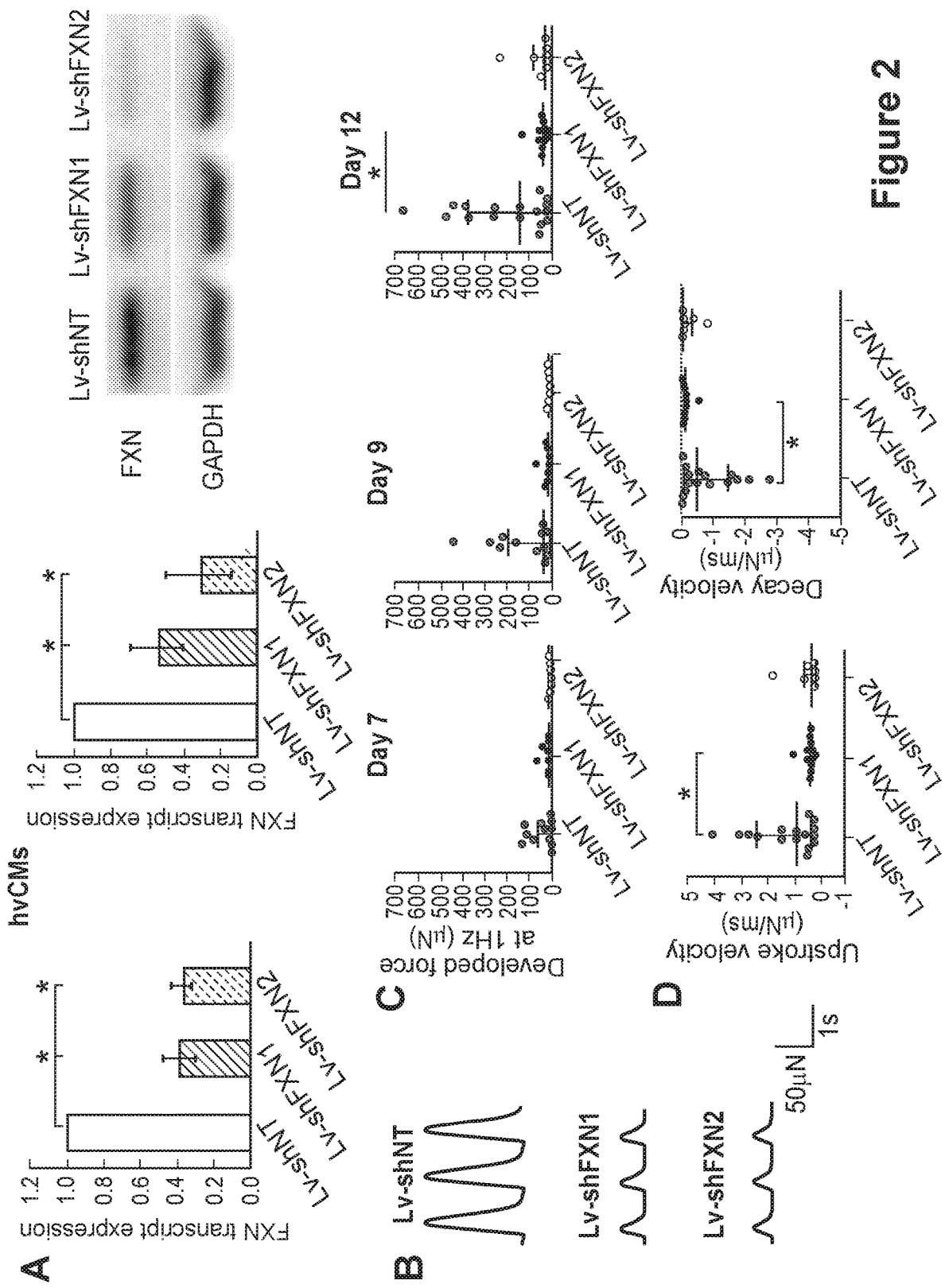
FIG. 2. Isogenic FRDA cardiac model derived from hESCs. A) FXN transcript and protein expression of hESC-hvCMs (normalized to GAPDH expression) transduced with Lv-shFXN1 (n=4) and Lv-shFXN2 (n=4), relative to control transduced with Lv-shNT (n=8). Data are shown as mean±SEM. B) Representative twitch force traces on day 12 for hES2-hvCTS transduced with Lv-shFXN1 and Lv-shFXN2, with Lv-shNT as control. C) Twitch force generation on days 7, 9, and 12 from 1 Hz-paced hESC-hvCTSs transduced with Lv-shFXN1 (n=14) and Lv-shFXN2 (n=7), compared to control transduced with Lv-shNT (n=17), shown as median with interquartile range. D) Kinetics analysis of hESC-hvCTS force generation on day 12. All force generation data are shown as median with interquartile range. * indicates statistical significance with p<0.05.

The disclosure provides a system and associated methods for screening compounds for beneficial or toxic cardiac effects in cardiomyocytes derived from patients having a neurological disease, disorder or condition that can have at least one cardiac effect. Typical configurations of the system involve an efficacy screen followed by a toxicity screen, depending on the phenotype of the disease being modeled. An initial efficacy screen is deployed to identify treatments that ameliorate, rescue or abolish disease symptoms, followed by a toxicity screen to eliminate treatments with deleterious side-effects. For modeling cardiac electrophysiology and arrhythmias, a Cardiac Anisotropic Sheet is provided, such as a human ventricular Cardiac Anisotropic Sheet (hvCAS) comprising a monolayer of human ventricular cardiomyocytes plated on microfabricated substrates, which provide environments conducive to the development of the anisotropic properties characteristic of human cardiac cells in vivo. Along with well-defined inclusion/exclusion quality-control criteria and algorithms, CAS platforms such as the hvCAS reproduce key electrophysiological features of the native human heart, while minimizing the variability commonly seen in conventional electrophysiological assays of hPSC-CMs for systematic assessments of disease- and drug-induced arrhythmogenicity. The bio-hybrid material provides the significant benefit of making available in vitro assays that more accurately reflect in vivo physiological effects. For assessing contractility, a multi-tiered system is employed, such as a two-tiered system and associated method with the first tier designed to provide an accurate yet rapid, versatile, and cost-effective initial screen of compounds for beneficial cardiac effects. The first-tiered system comprises a Cardiac Tissue Strip (CTS), such as a human ventricular Cardiac Tissue Strip (hvCTS) supported in a manner that allows for significant flexibility in movement of the gel, with an associated detection (e.g., recording) device to capture gel movement in the presence or absence of a test compound. The CTS is simple to prepare and is used in a straightforward method for screening compounds for the capacity to induce cell-embedded gel movement. The first-tier system and method are amenable to high-throughput formats as well as conventional formats.

A second tier screening system and method involves a tissue or organoid developed and maintained in an organoid cartridge or chamber typically located in an organoid module, as described herein. The second tier screen involves exposure of a tissue or organoid to a candidate compound in a cartridge or chamber placed in an environment where a detection (e.g., recording) device can monitor organoid behavior. The environment also typically provides for the delivery and removal of fluid such as media and compound-containing fluid under controlled conditions, with various controls needed to maintain an environment compatible with tissue or organoid viability. The two-tiered system is used in a two-tiered method that reveals compounds having beneficial cardiac effects at the cellular, tissue and/or organoid or organ level, increasing the accuracy and reliability of results obtained in screens for compounds having such effects. Moreover, the disclosure provides for a three-tier system and method involving the above-described two-tier system and method, supplemented by a third-tier system and method involving a multi-organoid (or multi-tissue or mixed tissue and organoid) module system and associated method. In this third tier, multiple tissues and/or organoids, which may be of the same type (e.g., cardiac) or different, are developed and maintained in distinct organoid cartridges or chambers that may conveniently be located in a single organoid module (it is understood that organoid cartridges and organoid modules may contain tissues or organoids). This typical arrangement conveniently allows for a single mirror system such as a pyramidal mirror system, to be used in conjunction with a single detection (e.g., recording) device. In subjecting a compound to the three-tiered system and method, information is obtained about the beneficial cardiac effects of the compound on cells as well as the effects of the compound on one or more cognate tissues, organoids or organs, or on a plurality of different tissues, organoids or organs. The three-tiered screening system and method further strengthen the data obtained in terms of accuracy, reliability and reproducibility, with a manageable addition to cost in terms of money and time.

The following quoted terms are expressly defined herein.

"APD50" means the action potential duration at 50% repolarization.

"APD90" means the action potential duration at 90% repolarization.

"FRDA" means Friedreich's ataxia.

"FXN" means the protein frataxin, while "FXN" means a polynucleotide encoding FXN.

An "engineered cardiomyocyte" is a cardiomyocyte that has been recombinantly engineered to exhibit a particular genotype and phenotype. As used herein, the typical engineered cardiomyocyte comprises a cardiomyocyte into which an exogenous nucleic acid, such as a short hairpin RNA against FXN, is introduced using any known vector, such as a lentiviral vector as disclosed herein.

"hESC" means a human embryonic stem cell, and "hESCs" means a plurality of human embryonic stem cells.

"hiPSC" means a human induced pluripotent stem cell, and "hiPSCs" means a plurality of human induced pluripotent stem cells.

"hPSC" means a human pluripotent stem cell, and "hPSCs" means a plurality of human pluripotent stem cells.

"hvCAS" means a human ventricular cardiac anisotropic sheet, and "hvCASs" means a plurality of human ventricular cardiac anisotropic sheets.

"hvCM" means a human ventricular cardiomyocyte, and "hvCMs" means a plurality of human ventricular cardiomyocytes.

"hvCOC" means a human ventricular cardiac organoid chamber, and "hvCOCs" means a plurality of human ventricular cardiac organoid chambers.

"hvCTS" means a human ventricular cardiac tissue strip, and "hvCTSs" means a plurality of human ventricular cardiac tissue strips.

In general, the disclosure contemplates neurological diseases or disorders, and ataxias, with cardiac dysfunction, e.g., neurological diseases or disorders that perturb the neurocardiac axis. Hereditary neurological diseases and disorders can have direct or indirect cardiovascular effects, including effects on the physiological functioning of the heart. Exemplary neurological diseases and disorders having the potential for such effects include, but are not limited to, Friedreich's ataxia (FRDA), as described herein; Kearns-Sayre syndrome, which is a mitochondrial myopathy with cardiac conduction abnormalities and cardiomyopathy; carbohydrate-deficient glycoprotein syndrome type Ia, which is a neurological disease with dysmorphy and cardiac manifestations (mean onset of cardiac involvement is 5 months, 20% die within first year of life, often due to serious cardiac complications); spinocerebellar ataxias, which have cardiovascular abnormalities, particularly abnormal heart rate variabilities; Wilson disease, which is a copper metabolism disorder with concentric remodeling and supraventricular tachycardia; arrhythmias; Dandy-Walker syndrome, which is characterized by cardiac malformations; dilated cardiomyopathy with ataxia, which exhibits DCM and long QT with 70% of patients progressing to cardiac failure or sudden cardiac death; Leigh disease, which is a neurological disorder that can be associated with hypertrophic cardiomyopathy; MELAS (mitochondrial encephalomyopathy, lactic acidosis, and stroke-like episodes), which is a mitochondrial disease with LV hypertrophy; MERRF (myoclonic epilepsy with ragged red fibers), which is a neuromuscular disorder with cardiomyopathy.

In order to sustain energy consumption required by constant cardiac contractions, cardiomyocytes—the individual working units of the heart—are endowed with the highest mitochondrial density of all cells.[26] FRDA, as an exemplary non-cardiac disease that has deleterious effects on the heart, is caused by a genetic mutation that decreases the production of FXN, and consequently biosynthesis of numerous iron-sulfur proteins that are critical for oxidative metabolism in the mitochondria. Consequently, the disease is expected to adversely affect cardiomyocytes, which depend predominantly on mitochondrial ATP production. Not surprisingly, heart failure and arrhythmia are the major causes of mortality in FRDA patients[3-6], indicating contractile and electrophysiological dysfunction at the cellular level. In the experimental work disclosed herein, the effects of FXN expression on contractile and electrophysiological function in hvCM models generated either from hESCs or hiPSCs were tested, with the hiPSCs including lines reprogrammed from FRDA-patient cells. Indeed, FRDA-hiPSC lines of two distinct patients both showed lower FXN transcripts and proteins than healthy hESCs and hiPSCs, indicating hvCMs from FRDA-hiPSCs provide a model for studying FRDA in vitro.

To eliminate possible differential responses in contractile and electrophysiological functions attributed to variations in genetic background from different hPSC lines, an isogenic FRDA model was generated by knocking down FXN expression in hESCs, using lentiviral delivered Lv-shFXN, to mimic the low FXN expression as reported in FRDA patients, as disclosed in the following examples. This strategy had proved to be effective, as demonstrated by reduction of FXN expression at both the transcript and protein level (FIG. 2A, Example 3). More importantly, for the first time, contractile dysfunction was observed in cardiac tissue hvCTS engineered from FXN-deficient hvCMs. Unlike healthy hESC-hvCTS that showed progressive increase in developed force over time, contractile force was reduced and remained low in FXN-deficient hESC-hvCTS (FIGS. 2B and 2C, Example 3). Moreover, the upstroke and decay velocities of force developed were also slower in FXN-deficient hESC-hvCTS. These observations suggest that the lack of FXN affected the ability of hvCMs to generate force, which became more obvious as the hvCTS matured over time.

Effects of FXN deficiency on cardiac contractile dysfunction were further validated in an FRDA-hiPSC-derived hvCM model. Similar to the isogenic FXN-deficient hESC-hvCM model, FRDA-hiPSC-derived hvCMs also demonstrated reduced synthesis of FXN by qPCR and Western blot, relative to healthy hiPSC-hvCM control, despite differences in genetic background between the cell lines. The relationship between developed force and FXN expression was validated by six different hESC- and hiPSC-hvCTS models for FRDA, including isogenic FXN knockdown models in healthy hESC- and hiPSC-hvCTSs, their respective healthy hESC- and hiPSC-hvCTS controls, and FRDA patient-derived hiPSC-hvCTSs from two patients. It is important to note the strong positive correlation between the magnitude of active force and FXN expression (FIG. 3B, Example 4), as indicated by Pearson's coefficient of 0.84, where a value of >0.5 indicates a strong positive correlation. Hence, the data disclosed herein establish, for the first time, the FRDA contractile phenotype in two types of in vitro models, i.e., an isogenic model from FXN knockdown and another model derived directly from an FRDA patient with an intrinsic mutation of the FXN gene.

Compromised contractility in FXN-deficient hvCTS could be attributed to either a decrease in the contractility of individual hvCMs or a reduction in the number of contractile cells. Since live-dead staining of hvCTSs did not show differences in the number of dead cells between FXN-deficient and healthy hvCTSs, loss of contractile hvCMs over time can be ruled out as the reason for reduced contractility in FXN-deficient hvCTS. Decrease in contractility of individual hvCMs is a reasonable expectation, as contraction is associated with high energy consumption, and FXN is needed for iron-sulfur proteins such as aconitase and succinate dehydrogenase that are involved in oxidative metabolism, which is the predominant method for ATP production in mature cardiomyocytes. Adverse effects on ATP production would be expected to result in compromised force generation.

FXN Deficiency Induced Electrophysiological Changes in hvCMs

Given that one of the main causes of mortality in FRDA patients is arrhythmia,[3-6] an extensive study was performed to determine the effects of FXN on electrophysiological properties in hvCAS, a monolayer of aligned hvCMs. This tissue configuration enables not only measurements of action potential parameters of individual cells, but also electrical conduction of these cells as a syncytium, which is the only way to truly test for arrhythmogenicity. Arrhythmogenicity was assessed by both the occurrence of automaticity and the incidence of reentry arrhythmia presented as spiral waves. While no statistically significant increase in arrhythmia was detected in FXN-deficient hvCAS compared to control, it is important to note that hvCASs were composed of ventricular CMs, whereas in FRDA patients, supraventricular arrhythmias are the commonly observed types of heart rhythm irregularities.

Figure 4:
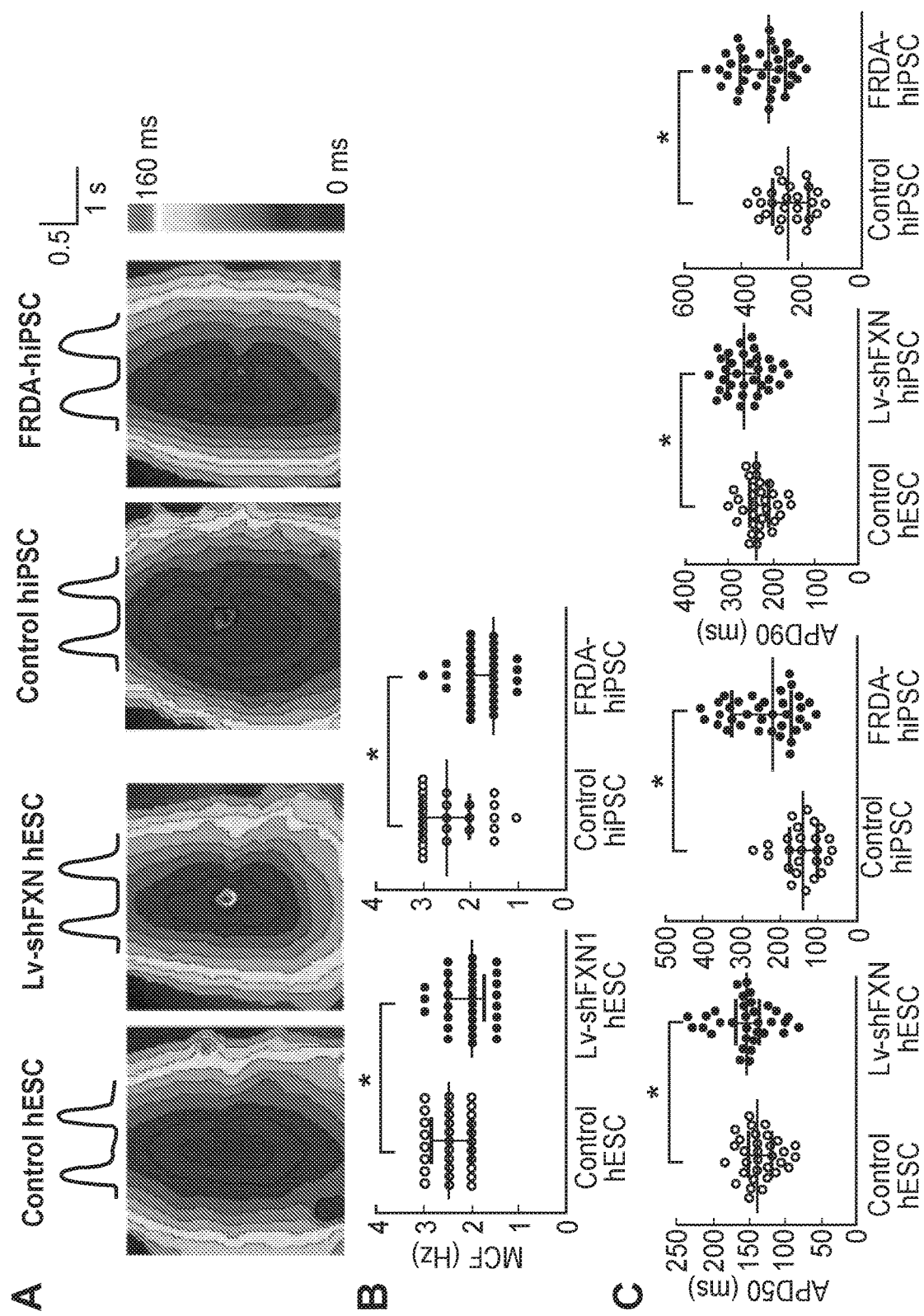
FIG. 4. Electrophysiological measurements from FXN-deficient hvCAS derived from hESCs and hiPSCs relative to their respective healthy controls. A) Representative action potentials and isochronal maps from control and Lv-shFXN-transduced hESC-hvCASs, and healthy control and FRDA patient-derived hiPSC-hvCASs. B) Maximum capture frequency (MCF) for control (n=32) versus shFXN (n=33) hESC-hvCAS and healthy control (n=25) versus FRDA (n=35) hiPSC-hvCAS. C) Action potential duration at 50% repolarization (APD50) and 90% repolarization (APD90) derived from optical mapping of control versus Lv-shFXN-transduced hESC-hvCAS and healthy control versus FRDA hiPSC-hvCAS. Data are shown as median with interquartile range. * denotes statistical significance with p<0.05.

Although no increase in arrhythmogenicity was detected in FXN-deficient hvCASs either transduced with Lv-shFXN or carrying a genetic defect in FXN, the average MCF of the cardiac tissue constructs was consistently lower for FXN-deficient hvCASs generated by either method when compared to their respective healthy controls (FIG. 4B, Example 5). MCF is an indicator of cellular connectivity—a low MCF in FXN-deficient hvCAS indicates a weak electrical coupling among these cells. Indeed, disrupted organization of connexin 43 that forms gap junctions at the intercalated discs has been observed in sections of cardiac tissue samples from FRDA patients.[27]

Interestingly, APD50 and APD90 were consistently prolonged in both isogenic FXN-deficient hESC-hvCAS and FRDA-hiPSC-hvCAS compared to respective control (FIG. 4C, Example 5). This result indicates that this disease phenotype is robust and unaffected by background genetic differences. Interestingly, the first sign of FRDA-associated pathological symptoms due to metabolic stress in the heart can be detected by abnormal electrophysiology, specifically the presence of a T-wave inversion in the EKG that reflects abnormal cellular repolarization.[6] This observation is in agreement with observed repolarization delay in FXN-deficient hvCASs. Delayed repolarization may be due to an increase in intracellular $Ca^{2+}$, which it is reasonable to expect as a result of reduced pump activity of sarco/endoplasmic reticulum $Ca^{2+}$-ATPase (SERCA) responsible for transporting $Ca^{2+}$ back into the sarcoplasmic reticulum (SR), thus affecting $Na^+$-$Ca^{2+}$ exchange across the sarcolemma. Consistency of APD prolongation across models indicates that APD parameters can serve as a robust readout for screening pharmacological treatment using a disease-in-a-dish model.

Restoration of FXN Expression Rescued Compromised Contractile Function

Figure 5:
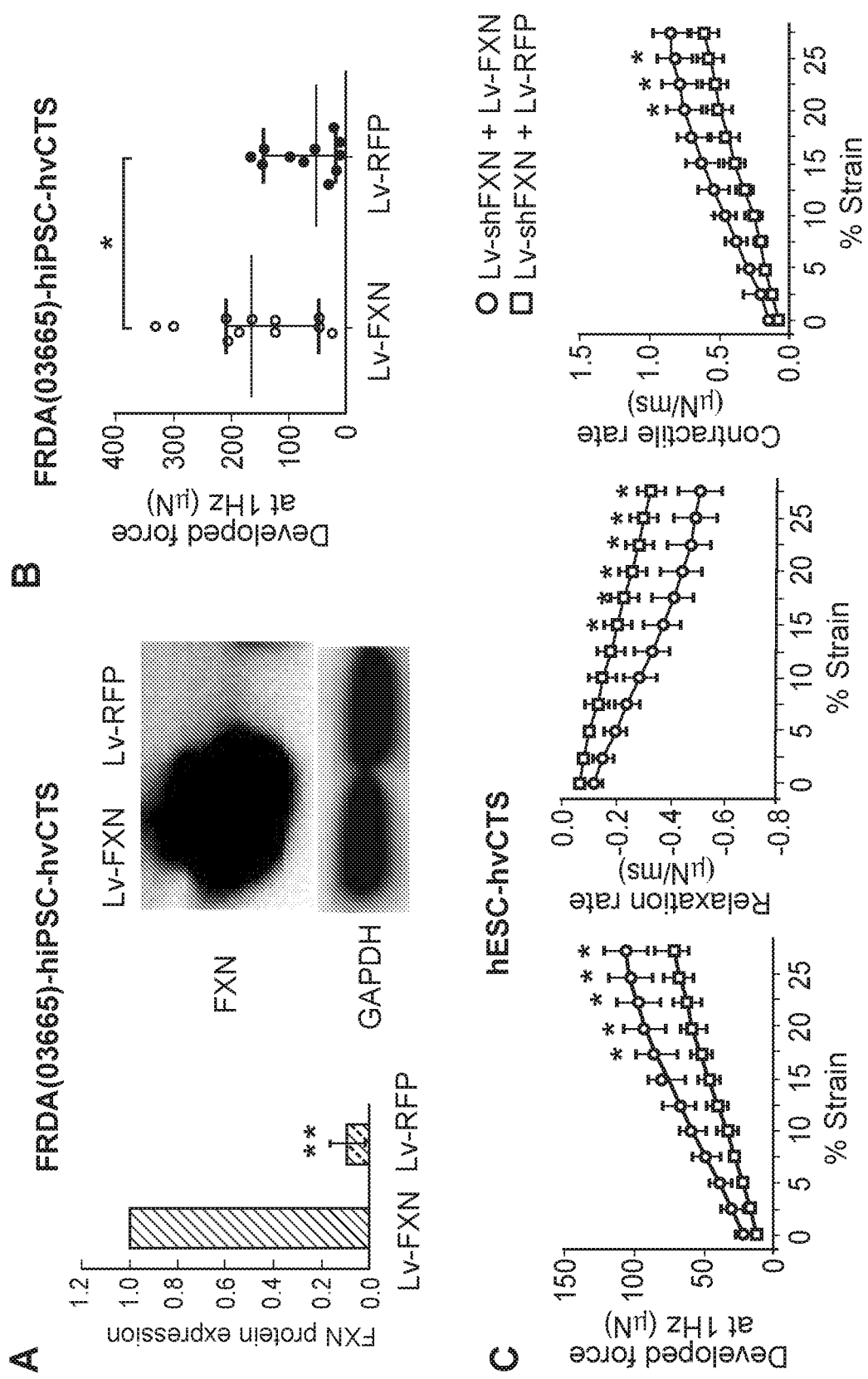
FIG. 5. FXN expression rescue of FRDA hvCTS model. A) FXN protein expression and representative Western blot image of FRDA(03665)-hiPSC-hvCMs transduced with Lv-RFP control (n=3) relative to rescue groups transduced with Lv-FXN (n=3). B) Twitch force generated at 1 Hz pacing in FRDA(03665)-hiPSC-hvCTS transduced with Lv-FXN (n=10) relative to Lv-RFP control (n=9). FXN expression data are shown as mean±SEM and force generation data are shown as median with interquartile range. * and ** denote statistical significance with p<0.05 and p<0.01, respectively. C) Isometric force measurement of hESC-derived hvCTS double-transduced with Lv-shFXN and Lv-FXN relative to control transduced with Lv-shFXN and Lv-RFP at 1 Hz (Lv-shFXN+Lv-FXN: n=17; Lv-shFXN+Lv-RFP: n=14). FXN expression data are shown as mean±SEM and force generation data are shown as median with interquartile range. * denotes statistical significance with p<0.05.

By inducing expression of FXN in FRDA-patient hiPSC and FXN-knockdown hESC FRDA models, the force generated in hvCTS from both models was significantly improved, demonstrating for the first time, rescue of compromised contractile function in human FRDA three-dimensional tissue models by restored expression of FXN (FIG. 5, Example 6). This is in agreement with the inducible and reversible murine FRDA model demonstrating restoration of FXN expression can reverse pathological effects.[16] These findings indicate restoration of FXN expression is an effective strategy for treating FRDA patient by preventing and reversing pathological cardiac symptoms that are major contributors to fatality for FRDA patients. Importantly, the work disclosed herein demonstrated that three-dimensional human pluripotent stem cell-derived tissues, with appropriate selection of sensitive readouts as had shown using an isometric force measurement system, serve as sensitive and accurate disease models for therapeutic testing and drug screening.

FXN-Deficient hvCOC Models

Figure 6:
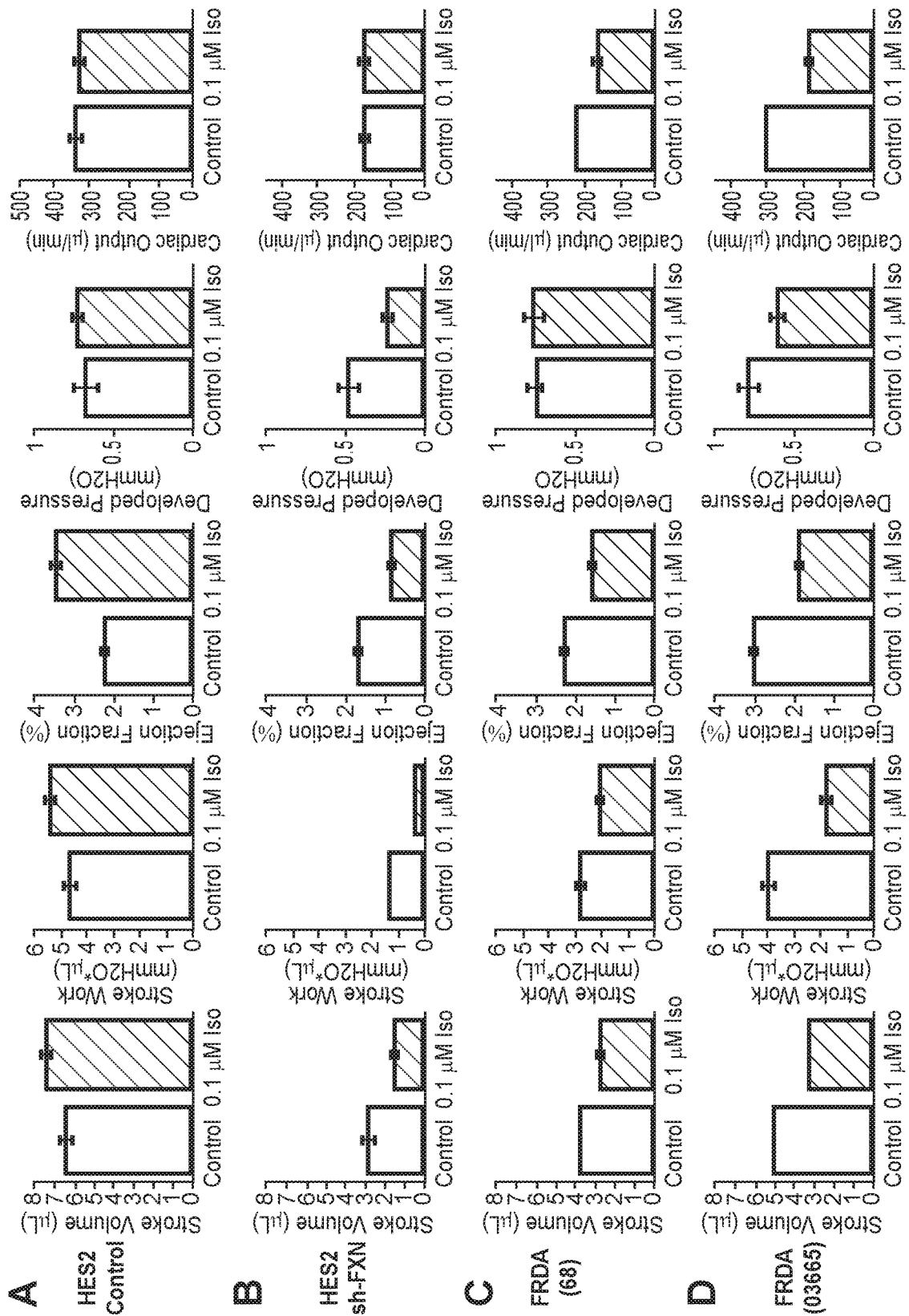
FIG. 6. FRDA hvCOC disease model. hvCOC FRDA models created with Lv-shFXN-transduced hESC-hvCMs, or patient-derived FRDA hiPSC-hvCMs, are physically intact and can pump fluid and generate pressure. These models can be cross-compared with healthy hESC-hvCMs in their functional properties, including stroke work, stroke volume, ejection fraction, developed pressure and cardiac output.

In addition to hvCTS, fluid-ejecting human ventricular cardiac organoid chambers (hvCOC) provides a higher-order engineered cardiac tissue for modeling FRDA disease phenotypes. The hvCOC model can recapitulate physiologically complex behaviors such as pressure-volume relationships, stroke work and cardiac output, and also provides a pro-maturation milieu to enhance the cardiomimetic properties especially as it relates to contractility. hvCOC FRDA models created with Lv-shFXN-transduced hESC-hvCMs, or patient-derived FRDA hiPSC-hvCMs, are physically intact and can pump fluid and generate pressure (FIG. 6). These models showed compromised functional properties, including stroke work, stroke volume, ejection fraction, developed pressure and cardiac output, when compared with control hESC-hvCOCs, both under baseline conditions or when treated with 0.1 µM isoproterenol, a known positive inotrope (FIG. 6). They add a higher-tier assay for treatments that produce positive results in the hvCTS disease models, providing a more physiological and mature tissue construct with higher sensitivity in confirming positive effects on contractility.

Current and Future State of In Vitro Cardiac Models for FRDA

For the experiments disclosed in the examples below, two types of human cardiac FRDA models using hESCs by FXN knockdown and hiPSCs reprogrammed from FRDA patient cells were developed. Each model has its own distinct advantage over the other. While generating an FRDA model through FXN knockdown from hESCs mimics FXN deficiency and creates isogenic diseased cells for comparison with healthy ones, thus reducing readout variabilities by eliminating differences in genetic background, an FRDA model generated from FRDA patient-derived hiPSCs is expected to be a more physiologically accurate cardiac disease-in-a-dish model in which FXN expression is suppressed by pathological GAA expansions in the FXN gene. This latter model is expected to be suitable for in vitro mechanistic studies of pathogenesis of FRDA. By utilizing isogenic and patient-specific FRDA models, we were able to determine robust contractile (developed force at pacing of 1 Hz) and electrophysiological (MCF and APDs) readouts, as indicated by consistent phenotypes exhibited in both types of FRDA models tested.

The experiments disclosed hereinbelow have demonstrated contractile and electrophysiological dysfunctions of cardiac tissues constructed from FXN-deficient hPSC-derived ventricular CM models engineered either from shRNA knockdown in healthy hESCs and hiPSCs or FRDA patient-specific hiPSCs, compared to respective controls. Specifically, reduction in force generation was detected in FXN-deficient hvCTS, and electrical coupling dysfunction and action potential prolongation were measured in FXN-deficient hvCAS, which reflect clinical symptoms of cardiomyopathy and T-wave inversion, respectively. Assessment of these parameters is expected to provide robust readouts for pharmacological screening using in vitro engineered cardiac tissue models for FRDA or other non-cardiac diseases capable of exhibiting deleterious cardiac effects. For diseases similar to FRDA, with both electrophysiological and contractile symptoms, efficacy and safety screening can be performed concurrently using both electrophysiological (hvCAS) and contractile (hvCTS/hvCOC) models.

Importantly, we have demonstrated in two human FRDA in vitro models that the pathological effects on cardiac contractile function associated with FXN deficiency are rescued by restoring FXN expression. This indicates that treatments which can stimulate FXN expression in patient hearts can rescue the contractile symptoms of FRDA, thus revealing a potential therapeutic strategy.

The following examples illustrate embodiments of the invention. Example 1 discloses the materials and methods used in the experiments disclosed herein. Example 2 shows that hiPSCs reprogrammed from FRDA patient fibroblasts exhibited reduced expression levels of FXN. Example 3 establishes that hESC-hvCMs with an isogenic FXN-knockdown exhibit reduced FXN expression and reduced contractile function. Example 4 shows that FXN-deficient hvCTS have reduced ability to generate contractile force. Example 5 reveals that FXN-deficient hvCAS exhibit altered electrophysiological properties. Example 6 shows that rescue of the FXN deficiency restores contractile force in hvCTSs. Example 7 shows FXN-deficient hvCOCs with contractile dysfunction as indicated by compromised stroke volume, stroke volume, developed pressure and cardiac output, both under baseline conditions and when treated with 0.1 µM isoproterenol.

Example 1

This example describes the Materials and Methods used in the experiments disclosed in the examples herein.
hPSC Culture and Differentiation into CMs Healthy hESC (HES2; ESI, NIH code ES02) and FRDA patient-specific hiPSCs (FRDA(68) and FRDA(03665), were cultured on hESC-qualified Matrigel (Corning) with mTeSR1 medium (Stem Cell Technologies), and hiPSC (PB02), reprogrammed from peripheral blood mononuclear cells by episomal nucleofection of transcription factors— OCT3/4, SOX2, KLF4, L-MYC, and LIN28—plus p53-interfering shRNA, was cultured on hESC-qualified Geltrex (Gibco) with Essential 8 medium (Gibco), at 37° C. with 5% $CO_2$. To differentiate hPSCs into cardiomyocytes, dissociated hPSCs were allowed to form cell clusters in mTeSR1 with 1 ng/ml bone morphogenetic protein 4 (BMP4) overnight in ultra-low-attachment plate and hypoxic condition. From day one to four, cell clusters were treated with 50 µg/ml ascorbic acid (Sigma-Aldrich), 10 ng/ml activin A, and 10 ng/ml BMP4 in StemPro-34 medium supplemented by GlutaMAX (Thermo Fisher Scientific) in hypoxic condition. Next, cell clusters in hypoxic condition were treated with 50 m/ml ascorbic acid and 5 mM IWR-1 in StemPro-34 medium until day 8. Cell clusters were maintained after day 8 in normoxic condition with StemPro-34 media containing 50 µg/ml ascorbic acid. Using this differentiation protocol[25], ventricular subtype yield of over 70% of hPSC-derived CMs was achieved. These differentiated cells are referred to as human ventricular (hv)CM and were used in all experiments disclosed herein.

Knockdown and Overexpression of FXN in hvCMs

To model FXN deficiency of FRDA in hESC- and hiPSC-derived vCMs, FXN was knocked down in both types of hvCMs by transduction with lentiviral shRNA (Lv-shFXN1: TRCN0000006137 or Lv-shFXN2: TRCN0000010996 inserts in pLK0.1 vector backbone) at multiplicity of infection (MOI) of 5 following the timeline in FIG. 1A. Respective control hvCMs were transduced with mammalian non-targeting shRNA (Lv-shNT). To restore FXN expression, FXN-deficient hvCMs were transduced with lentivirus to overexpress FXN (Lv-FXN; GE Dharmacon OHS5835-EG2395), with lentivirus delivering red fluorescent protein (Lv-RFP) serving as control. To assess and compare the electrophysiological and contractile functions among healthy, FXN-deficient and/or FXN-overexpressing hvCMs, two tissue construct platforms were constructed from these cells, each specifically designed to enable functional assessment, as described below.

Contractile Assessment of Human Ventricular Cardiac Tissue Strips (hvCTSs)

To assess contractile function through measurement of force generation, hvCMs were evaluated in the form of hvCTSs, as previously described.[23-24] Briefly, cardio-clusters from day 15 of hPSC cardiac differentiation were dissociated into single cells and allowed to recover in the incubator for 3 days before construction into hvCTSs. Each hvCTS consisted of $1.3 \times 10^6$ cardiac cells differentiated from hPSCs and $1.3 \times 10^5$ human foreskin fibroblasts in 40% 5 mg/ml collagen I (Thermo Fisher Scientific), 10% 9.3 mg/ml Matrigel, 6% 10×PBS, 2% 1 M NaOH, 8% 10× Minimum Essential Medium (Sigma-Aldrich), 8% 0.2 M HEPES, 10% hvCTS maintenance medium (Dulbecco's Minimum Essential Medium with 10% newborn calf serum), and sterile water to a final volume of 100 µl. The cell-collagen mixture was added to polydimethylsiloxane (PDMS) molds, with a force-sensing cantilever post at each end of the strip, to form hvCTS. The hvCTSs were maintained in DMEM medium supplemented with 10% newborn calf serum (Gibco).

Force generated by the hvCTS was measured at 37° C. in phenol red-free DMEM medium with HEPES using a custom-designed force measurement system that records displacement of the cantilever posts. hvCTSs were paced by electrical field stimulation to measure force-frequency response. An overview of the experimental timeline is shown in FIG. 1A.

Electrophysiological Assessment of Human Ventricular Cardiac Anisotropic Sheets (hvCASs)

To assess the electrophysiological properties of hvCMs as an aligned and electrically coupled syncytium with an anisotropic conduction property similar to ventricular CMs in vivo, cardio-clusters from day 20 of hPSC cardiac differentiation were dissociated into single cells, and $4.5 \times 10^5$ cells per $cm^2$ were plated as a monolayer on Matrigel-coated, microgrooved substrates fabricated from polystyrene shrink film (Shrinky Dinks 'Crystal Clear', K&B Innovations), with groove width of 15 μm, groove depth of 5 μm, and inter-groove distance of 5 μm, to form hvCAS, as previously described.[20] After allowing recovery for 8 days, action potentials of hvCASs were optically mapped with a MiCAM ULTIMA imaging system (SciMedia) using voltage-sensitive fluorophore Di-8-ANEPPS with Pluronic F-127 (Thermo Fisher Scientific) in Tyrode's solution containing blebbistatin (Sigma-Aldrich). Automaticity, threshold voltage, and maximum capture frequency (MCF) were first determined for each hvCAS, followed by programmed electrical stimulation to test for reentrant arrhythmias. An overview of the experimental timeline is shown in FIG. 1A.

Disease Modeling with Human Ventricular Cardiac Organoid Chambers (hvCOCs)

To assess cardiac function in a three-dimensional cardiomimetic configuration, hvCMs were evaluated in the form of hvCOCs, as previously described[49]. Briefly, cardio-clusters from day 15 of hPSC cardiac differentiation were dissociated into single cells and allowed to recover in the incubator for 3 days before construction into hvCOCs. Each hvCOC consisted of $1 \times 10^7$ hvCMs and $1 \times 10^6$ human foreskin fibroblasts in 40% 5 mg/ml collagen I (Thermo Fisher Scientific), 10% 9.3 mg/ml Matrigel, 6% 10×PBS, 2% 1 M NaOH, 8% 10× Minimum Essential Medium (Sigma-Aldrich), 8% 0.2 M HEPES, 10% hvCOC maintenance medium (Dulbecco's Minimum Essential Medium with 10% newborn calf serum), and sterile water to a final volume of 1 ml. The ice-cold sterile tissue mixture was transferred into a custom-designed bioreactor. The entire device was incubated for two hours at 37° C. and 5% $CO_2$ to initiate gel polymerization, then immersed in hvCOC maintenance medium. The tissue was maintained in this environment for 10 days at 37° C. and 5% $CO_2$, with daily half-media changes, during which time the tissue compacted around the balloon core to form a hollow human engineered cardiac organoid.

After 10-12 days in culture, the silicone balloon was deflated and carefully removed from the inside of the organoid. A high-sensitivity pressure catheter (Millar) was advanced into the lumen of the hvCOC chamber, and the catheter entry point was sealed. A high-speed camera (Allied Vision, Exton, PA, USA) was mounted outside of the bioreactor and permitted direct tissue monitoring with images acquired at 100 frames/second. Chamber pressure and digital video were acquired simultaneously using a custom acquisition program built in LABVIEW (National Instruments, Austin, TX, USA) and chamber cross-sectional area was extracted from the video using a custom script in MATLAB (MathWorks, Natick, MA, USA). Chamber volume was then estimated by assuming an equivalent sphere with the same cross-sectional area. From the resulting P-V loop, stroke work was calculated as the product of developed pressure and stroke volume. When required, electrical field stimulation was induced with a pair of carbon electrodes spaced 19 mm apart using a stimulation pulse width of 50 ms at 10V amplitude. Both pressure and video signals were passed through a digital low pass filter with a 13-Hz cut-off frequency in MATLAB prior to data analysis. hvCOC contractions were measured during spontaneous beating and electrical field stimulation at 1.0 Hz.

Example 2 hiPSCs Reprogrammed from FRDA Patient Fibroblasts Exhibited Reduced FXN Expression FXN expression was assessed for one healthy hESC, one healthy hiPSC, and two FRDA-hiPSC lines—FRDA(68) and FRDA(03665)—reprogrammed from two patients. FXN at the transcript level was comparable for the two FRDA-hiPSC lines, with both expressing >50% lower FXN than the healthy hESC and hiPSC lines (FIG. 1B). The protein level of FXN was in agreement with the transcripts, with FRDA-hiPSCs expressing the lowest level of FXN relative to the healthy hPSC lines. The expression difference was statistically significant for both FRDA lines compared to hESCs and for FRDA(68) to hiPSCs (FIG. 1B).

Example 3

Isogenic FXN-Knockdown Model Generated from hESC-hvCMs Exhibited Reduced FXN Expression and Contractile Function To model and study the progression of FRDA in isogenic human CMs in vitro, hESC-derived hvCMs were transduced with two Lv-shFXN constructs, Lv-shFXN1 and Lv-shFXN2, with non-targeting Lv-shNT transduction as control. Both Lv-shFXNs successfully induced knockdown of FXN at the transcript level, as demonstrated by reduction in hESC-hvCM expression levels of about 70% relative to Lv-shNT-transduced control (FIG. 2A). The reduction in FXN protein in hvCMs was 60% and 80% by Lv-shFXN1 and Lv-shFXN2, respectively. Of note, Lv-shFXN-transduced hvCMs exhibited reduction in FXN expression relative to the healthy hESC group that were comparable to the reduction in FXN expression in FRDA-hiPSCs compared to their respective healthy controls (FIG. 1B).

Contractile function was assessed as developed twitch force generation during pacing at 1 Hz. hvCTSs typically re-established spontaneous contractions within 6-7 days post-construction. Twitch force generation under 1 Hz electrical pacing was measured from the hvCTSs on days 7, 9, and 12 after hvCTS construction (FIGS. 2B and 2C). Contractile force in control hESC-hvCTSs progressively increased from a median of 5 μN on day 7 to 135 μN on day 12. Conversely, hESC-hvCTSs with FXN knockdown by either Lv-shFXN failed to significantly increase in developed force over time. By day 12, the median force in FXN-deficient hvCTS was 75-80% lower than that of control (FIG. 2C).

Example 4

Contractile Force Generation was Reduced in FXN-Deficient hvCTS

Figure 3:
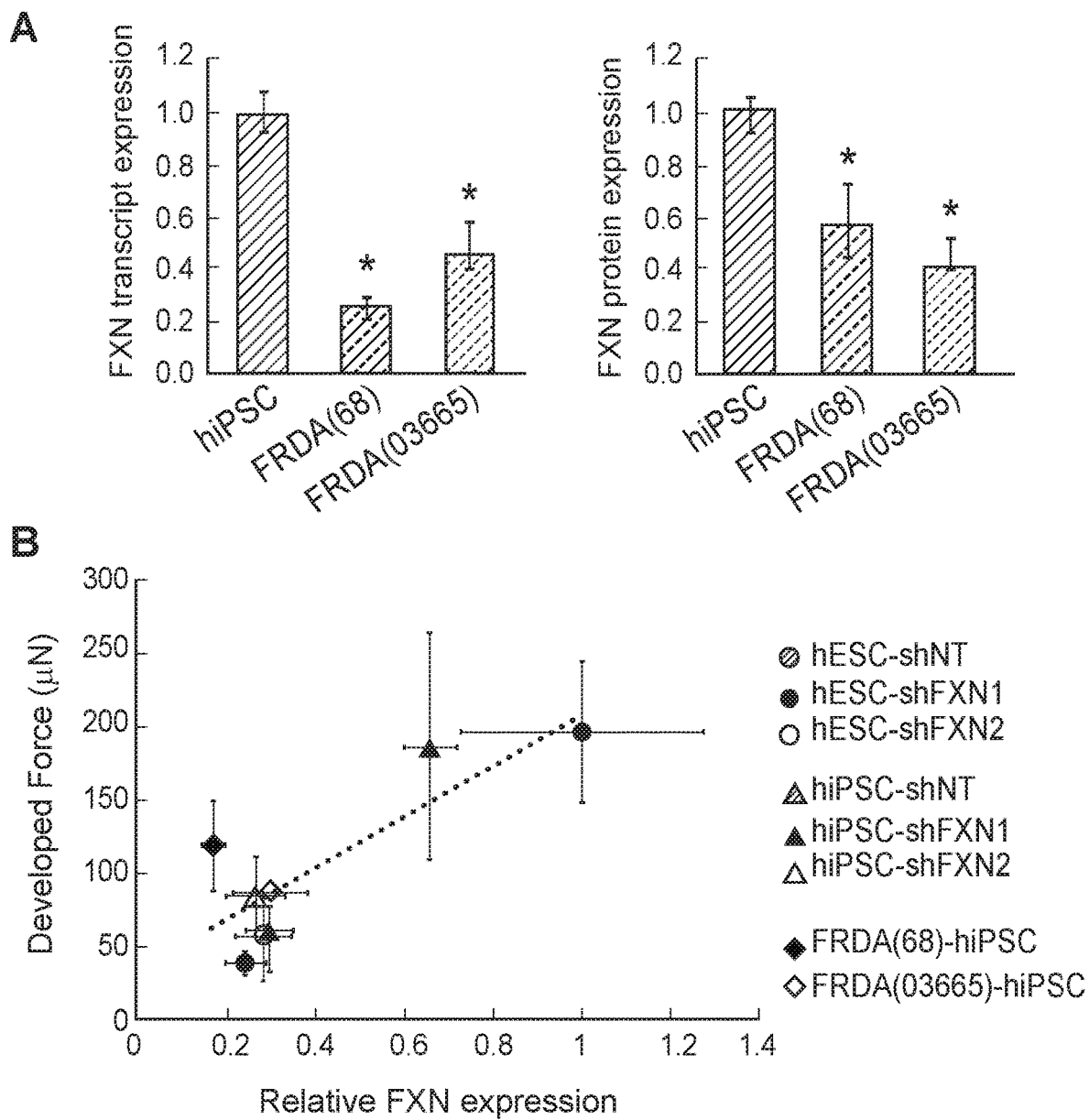
FIG. 3. FRDA cardiac model derived from FRDA-hiPSCs. A) FXN transcript and protein expression (normalized to GAPDH expression) of healthy control hiPSC-hvCMs (n=5), FRDA(68)-hiPSC-hvCMs (n=4), and FRDA(03665)-hiPSC-hvCMs (n=4). B) Correlation of developed force to FXN expression in hESC- and hiPSC-hvCTS (on day 12, at 1 Hz pacing). Data are shown as mean±SEM. * indicates statistical significance with p<0.05.

FXN expression was assessed at both the transcript and protein levels for hvCMs derived from FRDA(68)-hiPSCs and healthy hiPSCs. hvCMs differentiated from FRDA(68)-hvCMs expressed about 50% less FXN at the transcript level and nearly 80% less at the protein level compared to healthy controls (FIG. 3A). Force was measured after construction of FRDA-hiPSC-hvCMs into hvCTS, again in comparison with healthy hiPSC control. To correlate magnitude of force generation to level of FXN expression, generated force in hvCTS on day 12 stimulated by 1 Hz pacing was plotted against FXN transcript expression (FIG. 3B). Generally, FXN-deficient hvCTS—either due to knockdown in healthy hESC- or hiPSC-derived cardiomyocytes or due to genetic defect in FRDA-hiPSC-derived cardiomyocytes—exhibited compromised force generation, developing less than half of the force as healthy controls that expressed robust FXN. Hence, there is a strong direct correlation between the level of developed force with FXN expression, as indicated by Pearson's coefficient of 0.81.

Example 5

Electrophysiological Properties were Altered in FXN-Deficient hvCAS

Electrophysiological function of hPSC-derived hvCMs that were FXN-deficient—either by knockdown (control hESC versus Lv-shFXN hESC) or reprogrammed from FRDA patient-specific somatic cells (control hiPSC versus FRDA-hiPSC)—was assessed by optical mapping as hvCASs. Action potentials and isochronal maps of hvCASs were derived from the optical recordings (FIG. 4A). The incidence of spiral conduction waves and automaticity, or spontaneous generation of action potentials, were not statistically different between hESC-hvCASs transduced with Lv-shFXN compared to control transduced with Lv-shNT. The maximum capture frequency (MCF) of Lv-shFXN-transduced hESC-hvCASs, with a median of 2.0 Hz, was statistically lower than control, with a median of 2.5 Hz (FIG. 4B). FRDA-hiPSC-derived hvCASs were similarly harder to capture at higher pacing frequency compared to control—the median MCF was 1.5 Hz for FRDA-hiPSC-hvCASs and 2.5 Hz for healthy hiPSC-hvCASs (FIG. 4B).

Action potential and conduction parameters quantified from the optical recordings revealed electrophysiological differences between healthy and FXN-deficient hvCASs (FIG. 4C). Action potential upstroke and decay velocities and conduction velocities in the longitudinal and transverse direction did not show consistent differences between FXN-deficient hvCASs and control for both the hESC and hiPSC groups. Action potential duration at 50% repolarization (APD50) and 90% repolarization (APD90), however, were significantly prolonged in hESC-hvCASs transduced with Lv-shFXN (APD50: 153 ms, APD90: 268 ms) relative to control (APD50: 138 ms, APD90: 236 ms) (FIG. 4C). Notably, APD50 and APD90 were similarly prolonged in FRDA-hiPSC-hvCASs compared to healthy controls (FIG. 4C).

Example 6

Rescue of FXN Deficiency Restored Contractile Function in hvCTSs

As a first step to assess whether restoration of FXN deficiency would rescue compromised contractile function in the hvCTS FRDA model, FXN was force-expressed by transduction with Lv-FXN in FRDA(03665)-hvCTS. FXN-deficiency in FRDA(03665)-hvCTS transduced with Lv-FXN was rectified as indicated by a greater than 30-fold higher expression of FXN transcript and protein compared to control transduced with Lv-RFP (FIG. 5A). Contractile kinetics and force developed at 1 Hz pacing in Lv-FXN-transduced FRDA(03665)-hvCTS on day 17 post-construction were significantly higher with a median contractile force of 167 µN compared to control of 53 µN (FIG. 5B).

Next, the functional consequences of restored FXN expression were assessed in the complementary isogenic hESC-hvCTS FRDA model, which included two double-transduced groups with combinations of FXN-knockdown and forced expression—the Lv-shFXN+Lv-FXN group with knockdown and forced expression of FXN and the Lv-shFXN+Lv-RFP group with FXN knockdown and RFP control (FIG. 5C). As expected, FXN protein expression was restored for hESC-hvCTS transduced Lv-shFXN+Lv-FXN, with the expression level significantly higher than Lv-shFXN+Lv-RFP control. Further detailed physiological isometric force measurements by controlling the muscle strip length in 0.225-mm (2.5% strain) step increments revealed that the developed twitch force, under 1 Hz pacing, increased in all hvCTS groups on day 18 post-construction with increasing muscle strip length, reaching higher twitch force at Lmax, the length at maximum twitch force. Similar to the FXN-rescuing effects observed in the FRDA-hiPSC model, the twitch force was significantly higher in the rescued hESC-hvCTS FRDA model with robust FXN expression at the physiological range of 17.5-27.5% strain, exhibiting a median force of 109 µN at Lmax compared to the FXN-deficient control at 50 µN. The force kinetics were also significantly faster in the hESC-hvCTS FRDA model with restored FXN expression, with a median contractile rate of 0.89 µN/ms compared to a control level of 0.42 µN/ms at Lmax and a median relaxation rate of 0.57 µN/ms compared to the control rate of 0.24 µN/ms at Lmax.

Example 7

Organoid Module

Figure 7:
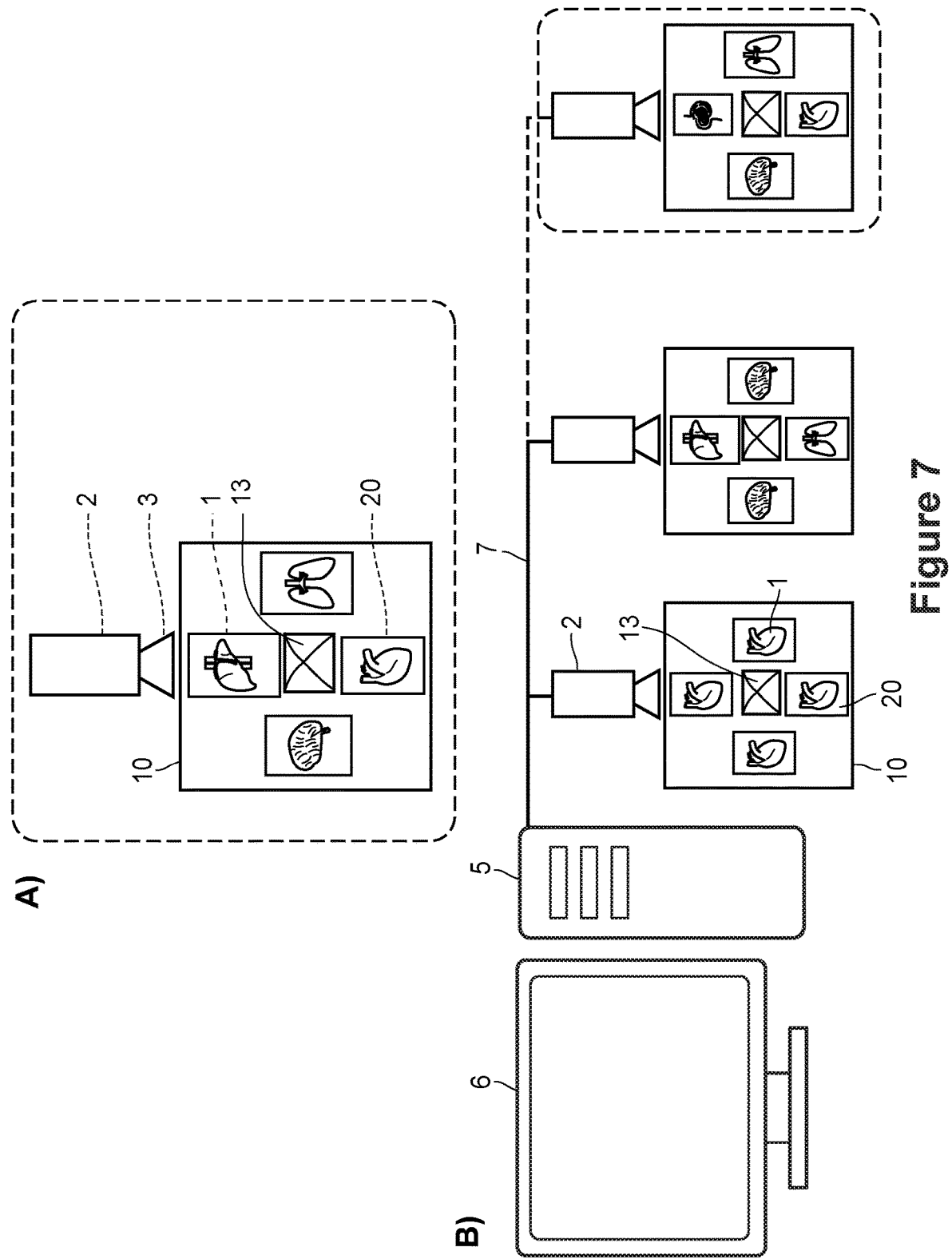
FIG. 7. A) A schematic illustration of a bioreactor system comprising an organoid module 10, a computer-controlled detection/recording device 2 (e.g., a camera) for simultaneously imaging up to four organoid cartridges 20 (and optionally saving the images), each containing an organoid 1 (at least one of which is a heart, whereas the others can be any organoid e.g., heart, brain, nerve, liver, kidney, adrenal gland, stomach, pancreas, gall bladder, lung, small intestine, colon, bladder, prostate, uterus, blood, vascular, tumor, eye, or skin), via reflective pyramidal mirror 13. An organoid module 10 may contain a multiple of the same type of organoid 1 or a variety of organoid 1 types. An organoid cartridge 20 is used interchangeably with an organoid chamber 20. B) A diagram of the imaging bioreactor platform consisting of a computer or data processor 5 controlling an array of organoid modules 10.

In some embodiments of the bioreactor disclosed herein, the enclosure (about 25×25×15 cm) is made of a sterilizable material with a detection/recording device 2, e.g., a camera, and a temperature control element 4, e.g., a heating unit, attached to the roof of organoid module 10, all as shown in FIG. 7. In some embodiments, the temperature control element 4, e.g., in the form of a heater, is placed within the enclosure. The vertical camera is focused onto a four-sided 45-degree pyramidal mirror 13 that reflects the side profile of one or multiple organoids 1 upwards to the camera. Angled LED lights 12 evenly illuminate the side profile of each organoid 1. Access doors allow interchangeable organoid cartridges 20 to simply be inserted into the organoid module 10 for monitoring and then taken out for other experimental analyses (e.g., optical mapping). After therapeutic administration to the organoid 1, the media 93 is mixed using a mixer 19 in the form of a miniature magnetic stirrer (e.g., ThermoSci Micro Stirrer) that can be switched on and off using software control. See FIG. 8. Each organoid module 10 is temperature-controlled using a temperature control element 4 comprising a thermostat, heater and fan (e.g., IncuKit Mini). $CO_2$ levels are also individually controlled at 5% for cell culture buffering. The platform's $CO_2$ control system comprises a single tank connected to a pressure regulator, routed to a solenoid valve manifold (e.g., Takasago CTV-2-4MIC) and finally a flowmeter (Dwyer Mini-Master Flowmeter) before connection to each organoid module 10. Each valve is individually controlled via a multichannel digital output module (e.g., NI-9472). A $CO_2$ sensor (e.g., SprintIR) within the enclosure measures the $CO_2$ level and controls the valve to switch between open and closed states. Additional sensors (e.g., 02 sensor) are contemplated for incorporation to further control specific partial pressures within the enclosed environment.

Microtissues are not ideal for emulating human organ response as they lack key features of larger organs, such as the diffusion limitations of thicker tissues. A bioreactor that permits fluidic exchange between multiple macroscopic organoids recapitulates critical physiological and pharmacological features of the human body. The ability to measure multiple functional properties in a simplified biomimetic model of the human body provides new avenues to bridge the long-standing gap between traditional cell culture systems, in vivo animal models and clinical trials. In combination with somatic reprogramming of induced hPSC, the "human-body-in-a-jar" system is expected to serve as a versatile platform for next-generation drug discovery, cardiotoxicity screening, disease modeling and other ethnicity-, sex- and patient-specific applications.

Data from the hvCOC FRDA disease model also reveals physiological distinctions between healthy cardiomyocytes and cardiomyocytes effectively derived from FRDA patients (FIG. 6). hvCOC FRDA models created with Lv-shFXN-transduced hESC-hvCMs, or patient-derived FRDA hiPSC-hvCMs, are physically intact and can pump fluid and generate pressure (FIG. 6). These models, when cross-compared with healthy hESC-hvCMs (transduced with a lentiviral non-targeting shRNA control), show compromised functional properties, including stroke work, stroke volume, ejection fraction, developed pressure and cardiac output, both under baseline conditions and when treated with 0.1 µM isoproterenol (iso) (FIG. 6).

Example 8

Screening Apparatus or Bioreactor

The disclosure provides a custom bioreactor used to culture many, and in some cases a variety of, tissue-engineered human organoids. The device was designed to allow interconnection and simultaneous measurement of multiple organoids, with features that enhance reproducibility and efficiency in organoid function testing by enabling subsequent characterizations to be performed within the same bioreactor with minimal manipulation or intervention by the operator.

FIG. 6 provides a high-level schematic view illustrating the versatility of the disclosed bioreactor system. FIG. 6A shows an organoid module 10 which contains at least one organoid cartridge 20. An organoid cartridge 20 contains a single organoid 1 of any type (e.g., heart, brain, nerve, liver, kidney, adrenal gland, stomach, pancreas, gall bladder, lung, small intestine, colon, bladder, prostate, uterus, blood, vascular, tumor, eye, or skin, and the like), preferably heart. An organoid module 10 may contain multiple organoid cartridges 20, and thus may contain multiples of a single type of organoid 1 or a variety of organoids 1. The organoid module 10 is oriented such that a detection/recording device 2, e.g., a camera, can detect and record the contents of the organoid module 10, such as by having a face of the organoid module 10 closest to detection/recording device 2, and preferably perpendicular to the device, be substantially or completely transparent to at least one wavelength of the electromagnetic spectrum detected by detection/recording device 2. FIG. 6B presents a data processor 5, e.g., a computer, in connection with at least one organoid module 10. The organoid modules 10 are typically in 1:1 correspondence with the detection/recording devices 2, and the detection/recording devices 2 are in electronic communication with data processor 5 via communication path 7, e.g., either conventional electrical wiring or by wireless communication. Video monitor 6 may also be connected to data processor 5 via communication path 7.

FIG. 7 presents a perspective view of an organoid module 10. Within organoid module 10 is located at least one organoid cartridge 20. Disposed within, or without (not shown), organoid module 10, and disposed within (not shown), or without, organoid cartridge 20 is mixer 19, such as a movable platform (e.g., shaker or rotating platform) on which organoid module 10 is placed or a magnetic stirring device (e.g., stir bar) located inside or outside organoid cartridge 20. In some embodiments, located within organoid module 10 is at least one light source 12 for illuminating organoid 1. Also located within organoid module 10 is at least one mirror 13 for directing electromagnetic radiation in the form of direct and/or reflected light images from organoid 1 to detection/recording device 2. In some embodiments, mirror 13 is a pyramidal mirror 13 to direct images from multiple organoid cartridges 20 to a single detection/recording device 2. A pyramidal mirror 13 can join the images of multiple organoid cartridges 20 into a single condensed viewpoint to maximize image resolution, while permitting the individual organoid cartridges 20 to be spaced physically apart from each other.

Figure 8:
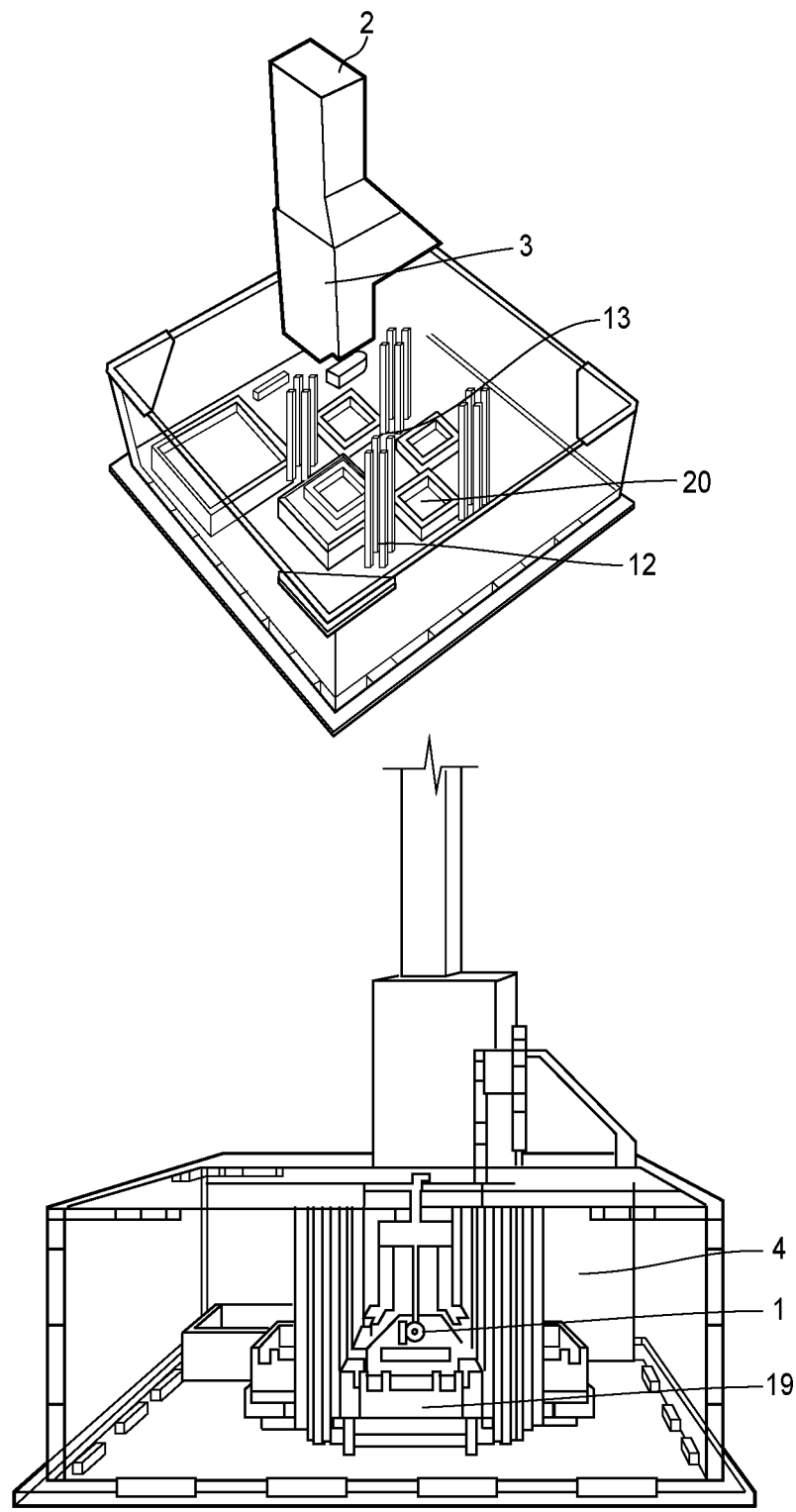
FIG. 8. Three-dimensional rendering of an organoid module 10 with four organoid cartridges 20. Isometric and side views are presented. Also shown is an organoid 1, a detection/recording device 2 connected to a lens 3, lights 12 (e.g., LED lights), a pyramidal mirror 13, an organoid cartridge 20, a temperature control element 4 (e.g., a heater), and a mixer 19, such as a stir bar.

FIG. 8 illustrates elements of an embodiment of the bioreactor system that are involved in fluid movements, e.g., media flow, particularly the fluid movements involved in adding, or feeding, fresh media and removing, or aspirating, spent, or waste, media. FIG. 8A illustrates the entirety of the fluidic exchange system for a single organoid cartridge 20 in organoid module 10, with FIG. 8B providing the combination of activated valves and pumps for aspiration and FIG. 8C providing the combination for feeding fresh media. The components of the system involved in fluid, e.g., media, movements can be located within, or without, organoid module 10. In describing an embodiment of the bioreactor system providing fluid movements as illustrated in FIG. 8, attention will be focused on FIG. 8B for media aspiration and on FIG. 8C for feeding of media to cells, tissues and organoids of the disclosure. It is understood that the combined descriptions of aspiration and feeding will provide a description of the complete fluid communications within an embodiment of the bioreactor system, as illustrated in FIG. 8A. In the remaining description of FIG. 8, attachments are to be understood as providing fluid communication between the attached components.

Turning now to the features of FIG. 8B involved in one embodiment of the bioreactor system for aspirating media, media 93 is in contact with cartridge media-junction D tubing 86, which is attached to junction D valve 67. Also attached to junction D valve 67 is organoid-junction D tubing 85. In addition, junction D valve 67 is attached to junction D-pump C tubing 87, which is attached to pump C 72. Pump C 72 is attached to pump C-junction C tubing 88, which is attached to junction C valve 66. Junction C valve 66 is attached to junction C-mix/recycle tank tubing 89, which in turn is attached to mix/recycle tank 73. In some embodiments, media 93 is recycled and routed towards mix/recycle tank 73. Junction C valve 66 is also attached to junction C-waste tubing 90 leading from junction C valve 66 to waste.

In operation, the feeding of cells of the organoid, involves components highlighted in FIG. 8C, including fresh media tank 60, which is attached to fresh media-junction B tubing 78, which in turn is attached to junction B valve 65. Junction B valve 65 is attached to junction B-pump B tubing 79, which is attached to pump B 71. Pump B 71 is in turn attached to pump B-junction E tubing 80, which is attached to junction E valve 68. Junction E valve 68 is also attached to junction E-junction F tubing 82, which is attached to junction F valve 69. Also attached to junction F valve 69 is cartridge media-junction F tubing 83, which also contacts cartridge media 93.

Additional attached components are described that provide fluid communication within the system and permit additional functions, including but not limited to, therapeutic additive dilution, perfusion of therapeutic(s), therapeutic washout of organoid, rinsing of fluidic lines, and the like. Fresh media tank 60 is attached to, and in fluid communication with, fresh media-junction A tubing 74, which in turn is attached to, and in fluid communication with, junction A valve 64, e.g., a three-way fluid controller or valve. Additive container 62, e.g., a therapeutic container, is used to deliver at least one therapeutic to additive tank 63, which is attached to additive tank-junction A tubing 75, which in turn is attached to junction A valve 64. Junction A valve 64 is also attached to junction A-pump A tubing 76, which is attached to pump A 70. Pump A 70 is attached to pump A-mix/recycle tank tubing 77, which is in turn attached to mix/recycle tank 73. In some embodiments, media from fresh media tank 60 is used to dilute therapeutic(s) from additive tank 63 within mix/recycle tank 73. Mix/recycle tank 73 is also attached to mix/recycle tank-junction B tubing 92, which in turn is attached to junction B valve 65. Junction E valve 68 is attached to junction E-organoid cartridge tubing 81. In some embodiments, media can be delivered through junction E-organoid cartridge tubing 81 to increase pressure within organoid 1. A pressure probe, i.e., pressure transducer 95, detects pressure, and changes in pressure, within an organoid 1 and converts the pressure to an analog electrical signal that is typically transmitted to the data processor, thereby allowing pressure to be monitored and adjusted by the system. In addition, the device provides for the washout or rinsing of fluidic lines. In particular, junction F valve 69 is attached to junction F-waste tubing 84, which in turn leads from junction F valve 69 to waste. In some embodiments, fluid can be removed from the fluid exchange system without coming in contact with organoid cartridge 20 by exiting to waste through junction F-waste tubing 84.

Figure 9:
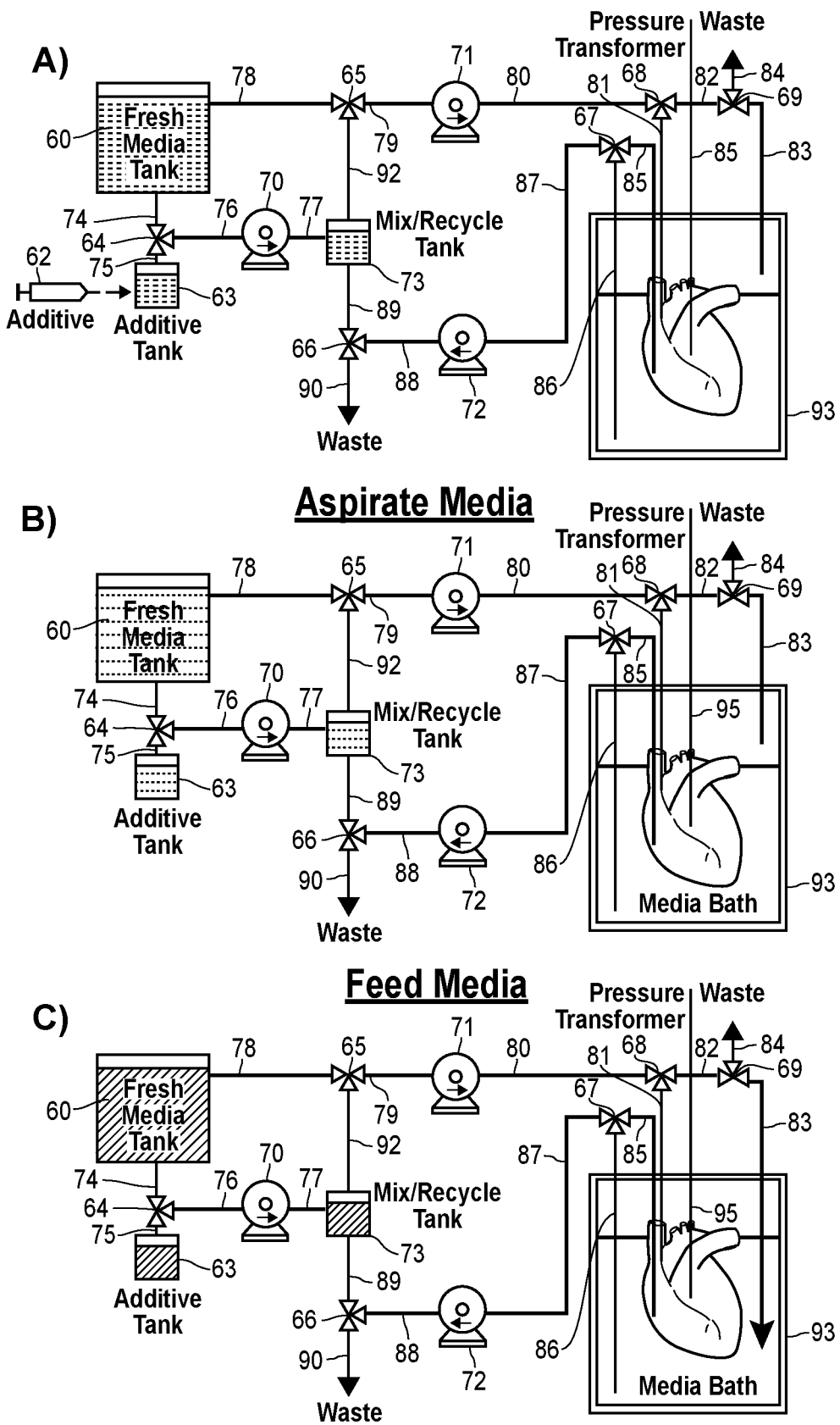
FIG. 9. A) Schematic of fluidic exchange system for an organoid cartridge, including fluidic lines, pumps, valves, pressure transducer and fluid tanks. Specific configurations of valves and pumps are used depending on the function, such as B) aspiration or C) fresh media addition to the media bath. A detailed description of the illustrated embodiment of the bioreactor system is presented in Example 6.

FIG. 9 presents a higher-level schematic of fluidic exchange within organoid module 10 to illustrate the creation of a "body-in-a-jar". FIG. 9A presents a fluidic exchange system that transfers media between at least two organoid cartridges 20 within organoid module 10. Fluid is directed through the system by a series of valves and pumps. FIG. 9B illustrates a fluidic exchange system where fluid is directed by valves and is pumped solely by a biological pump (e.g., a heart organoid 1), thereby providing a self-powered "body-in-a-jar".

Figure 10:
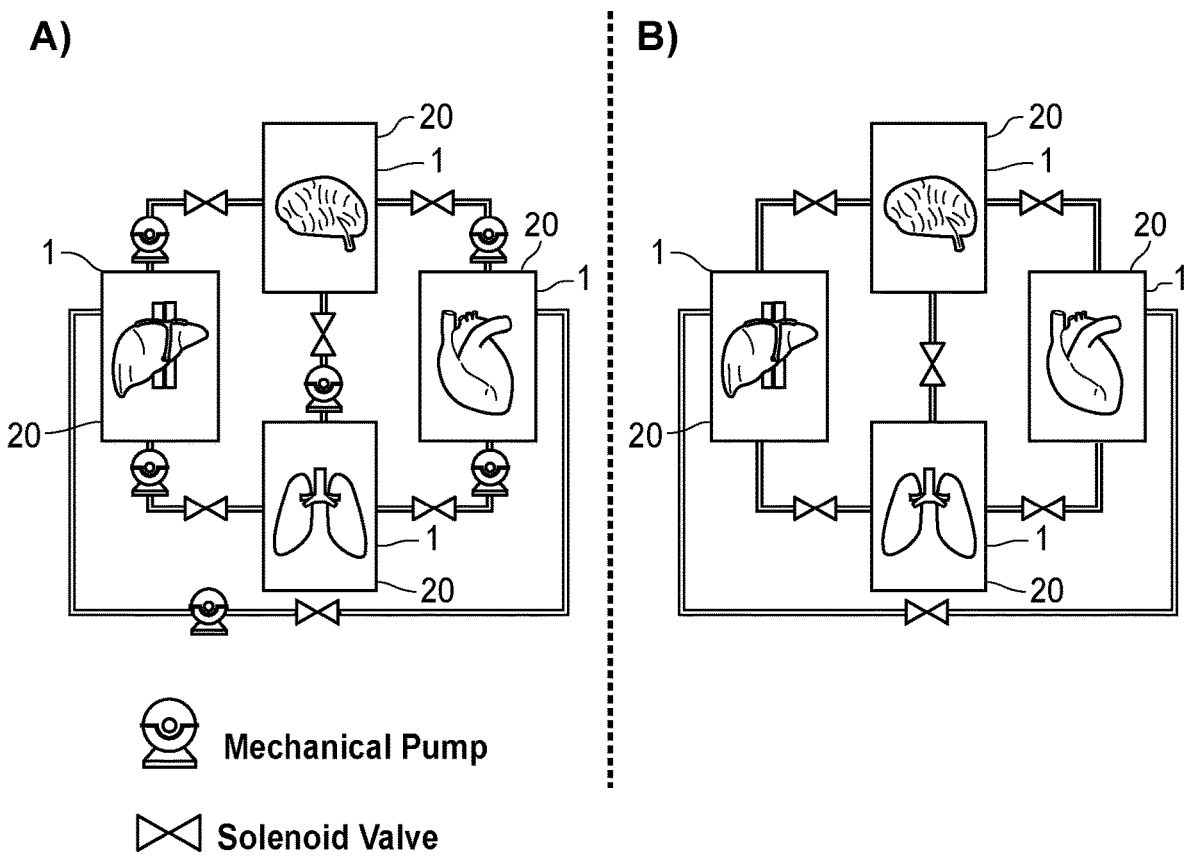
FIG. 10. A) Graphical representation of fluidic exchange system consisting of fluidic lines, pumps, and valves that direct media between multiple organoid cartridges within a module. A variety of organoid types can be connected to simulate a "body-in-a-jar". B) A heart organoid with sufficient pumping ability could be utilized as the sole biological pump to form a self-powered "body-in-a-jar". Example 6 provides additional description of these embodiments of the bioreactor system.

FIG. 10 presents methods of flowing fluid into and out of organoids 1. FIG. 10A illustrates an organoid 1 (left panel: heart organoid; right panel: liver organoid) connected to media inlet tube 26 and media outlet tube 28, which permits fluid to be directed into the void of the organoid 1 and out through media outlet tube 28 to a waste path. The direction of fluid flowing through the organoid 1 is controlled by inlet valve 27 and outlet valve 29. FIG. 10B represents a method of applying mechanical pressure to an organoid 1, such as a lung organoid 1. A fluidic pump controls fluid flow (e.g., gas or liquid) to organoid 1 and modulates the pressure of the organoid cavity to control the size of organoid 1. Absolute pressure values depend on the material properties of the organoid 1 and the desired size of the membrane for a given application. Applied relative pressures are adjusted for mechanical strain up to 25%.

As would be apparent to those in the field, some features of the bioreactor are optional and most of the features exist in a variety of embodiments. In some embodiments, cells can be sourced from any mammalian species or engineered as organoids 1 from cells and/or extracellular matrix. Any organ tissue type is suitable for use in the disclosed system, compositions and methods; heart cells, tissues and organoids are preferred. For example, tissues can act as surrogates for any organ, including but not limited to the heart, brain, nerve, liver, kidney, adrenal gland, stomach, pancreas, gall bladder, lung, small intestine, colon, bladder, prostate, uterus, blood, vascular, tumor, eye, and skin.

Organoid cartridge 20 containing organoid 1 is typically a cube made of a transparent solid that can be disposable or sterilizable, with at least two access ports such as doors. Suitable transparent solids include glass, and clear plastics such as polystyrene, acrylic and polycarbonate. Organoid cartridge 20 can also be any polygonal shape provided that detection/recording device 2 can detect and record the behavior of cells in organoid 1 within organoid cartridge 20. Given that the structure of organoid cartridge 20 is limited by the need to allow detection/recording device 2 to detect cell behavior, it is apparent that a variety of transparent and translucent materials may be used in constructing organoid cartridge 20. Even opaque materials are envisioned in embodiments where detection/recording device 2 is not detecting the transmission of visible light from organoid 1. Organoid cartridge 20 is also constructed to be fluid-tight, thereby allowing organoid cartridge 20 to contain cartridge media 93 to feed the cells of organoid 1. Also, a cartridge lid can provide apertures for penetration of at least one electrode or a pressure probe, i.e., pressure transducer 95.

At least one organoid cartridge 20 is contained in an organoid module 10, which is formed from materials similar to the materials used for organoid cartridge 20. Organoid modules 10 are typically square or rectangular in plane view, and typically contain a top in addition to a bottom. Organoid modules 10 are sized to accommodate at least 1, 2, 3, 4, 5, 6, 8, 10, or more organoid cartridges 20. The walls, top and bottom of organoid module 10 are typically formed of a transparent solid such as glass or a clear plastic (e.g., acrylic or polycarbonate), but may also be formed of translucent or opaque materials provided that detection/recording device 2 can detect, and record, cell behavior. Organoid module 10 also typically contains one or more light sources 12, and one or more mirrors 13, such as a pyramidal mirror 13. In several embodiments, there is at least one light source 12 and at least one surface of a mirror 13 for each organoid cartridge 20 contained in an organoid module 10.

Remaining components of the system include tanks, such as fresh media tank 60, mix/recycle tank 73, and additive tank 63, which are vessels for containing fluids used in the bioreactor. Such tanks can be any of a variety of dimensions and made from any of a number of materials, provided that the tanks as constructed can be used in an environment designed to minimize biological contamination, such as a sterile environment, and provided that the material used is compatible with any fluids it may contain and with the creation of one or more ports for fluid movement. Embodiments of the bioreactor may also involve one or more pumps, such as pump A 70, pump B 71 and pump C 72, and such pumps can be the same or different and can operate on any principle known to provide for the movement of fluids such as air and/or media through tubes. Exemplary pumps include peristaltic pumps, siphon pumps compatible with sterile environments, positive-displacement pumps such as piston-driven pumps, and non-positive-displacement pumps such as centrifugal pumps. In some embodiments, gravity is used to move fluids and no pumps are used to move, e.g., media.

Organoid module 10 also can interface with various tubes to move gas, such as air, used to provide pressure, e.g., inflate an organoid, which can be a balloon (e.g., a 6-Fr silicon Foley catheter balloon) or to move fluid. Pressure variations sufficient to control the inflation of a balloon or to move fluid in the system are achieved at pressures compatible with the use of a wide array of tube types and not just tubing certified to handle high pressure. For example, clear, plastic, flexible tubing is suitable for use, such as Tygon® tubing. Moreover, the various tubes can be combined into a single run of tubing as noted above, and such combined tubing is particularly well-suited for use with peristaltic pumps. Additionally, the tubing used in a given embodiment can vary in composition, internal diameter and external diameter. Another feature of the system are the junctions. Junctions typically are connected or attached to two or three tubes, which can vary in diameter and composition, as noted above. These junctions can be mere conduits or, more typically, are valves capable of directing the flow of fluid such as media from any attached tube to any other one or two other attached tubes. Additional features and variations thereof will become apparent from the entirety of the disclosure provided herein.

In some embodiments, the organoid model has inflow and outflow fluid pathways (FIG. 10A). Valves (e.g., check valves, solenoid valves) control the direction of fluid movement in and out of an organoid with a cavity. In some embodiments, a single shaft or tube for inflow and outflow is contemplated (FIG. 10B). A fluidic pump controls fluid flow rate into and out of the organoid. In some embodiments, unequal inflow and outflow fluid rates are used to control the amount of fluid within the organoid. Adjusting the volume within the organoid cavity results in mechanical stretch in pliable organoids. In some embodiments, stretch is applied as a step function (passive stretch) or a sigmoidal function (cyclic stretch). Mechanical stretch is considered to be a mechanotransduction signal in many organoid types. In some embodiments, a combination of mechanical and electrical stimulation presents a more robust response for therapeutic screening.

A fluidic exchange system automates routine media changes, adjusts intraluminal pressure, perfuses candidate therapeutics during screening, and exchanges media between organoids (FIGS. 8 and 9). The fluidic system consists of a series microfluidic pumps, 3-way valves controlled by a digital output board, and media reservoirs. Changing the valve configuration alters the direction in which media travels. In some embodiments, fluid can be added to, or removed from, a hollow vertical mounting shaft to which an organoid is connected, thus adjusting the hydrostatic pressure. A pressure transducer 95 and signal conditioner (e.g., OPP-M and LifeSens) senses the mean pressure within the organoid and communicates with the pumps via LabVIEW to adjust for a desired intraluminal pressure. Additionally, the fluidic exchange system is used for mixing and perfusion of compounds to the organoid. A solution is pumped from the additive tank and mixed with the circulating media. The compound then perfuses into organoid cartridge 20 and through organoid 1, similar to drug delivery via blood flow in humans. In some embodiments, the fluidic system of pumps and valves connects at least two organoid cartridges 20 within an organoid module 10 to permit exchange of media and/or therapeutic(s) between or among the organoids 1. Additionally, in some embodiments the fluidic exchange system between organoid cartridges 20 is powered by a biological pump in the form of an organoid 1, such as a cardiac organoid 1.

Example 9

Bioreactor Controls.

Figure 11:
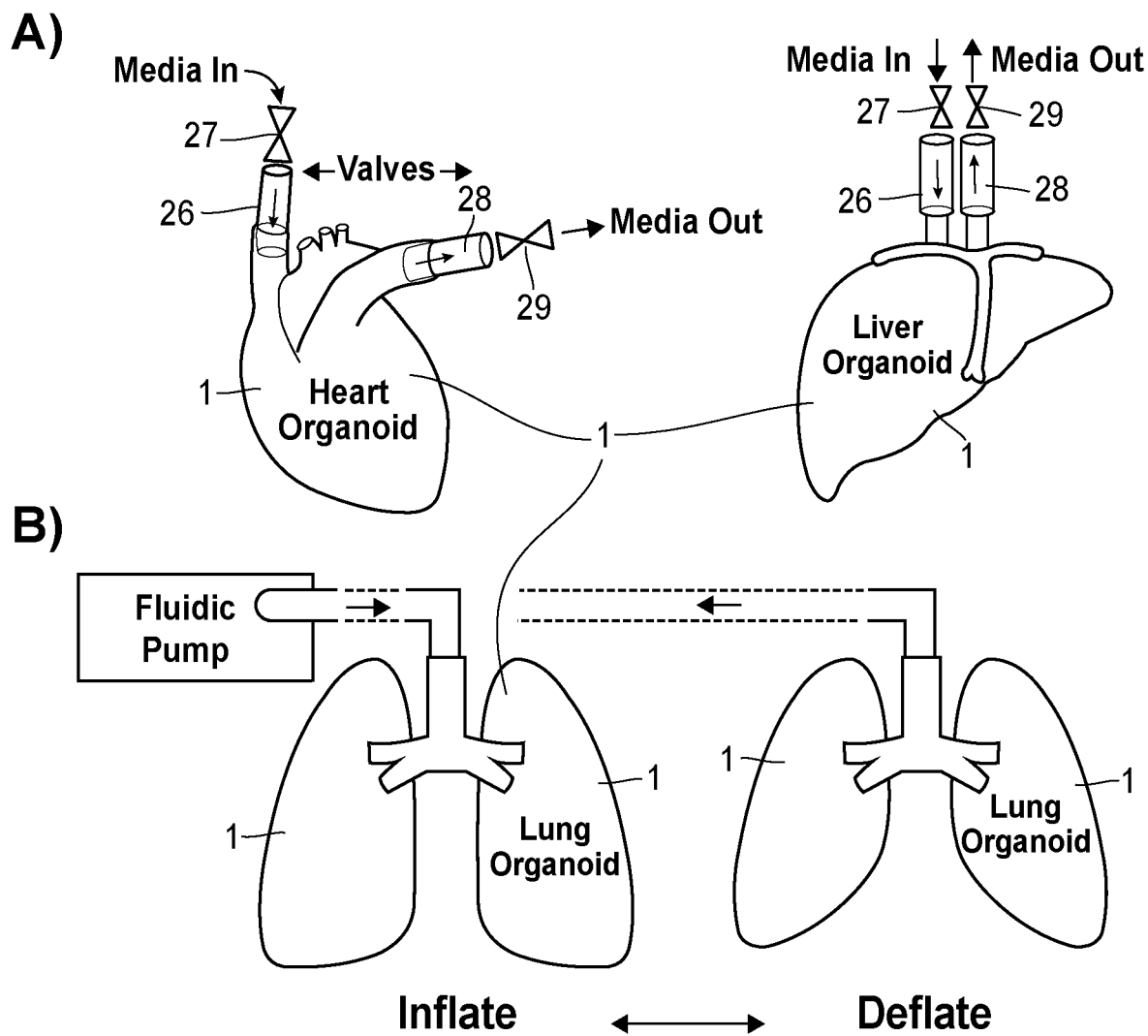
FIG. 11. A) An embodiment of the bioreactor system is illustrated that shows inlet and outlet pathways for media exchange through an organoid 1 controlled by valves (left pane: heart organoid; right pane: liver organoid). B) Schematic of mechanical stimulation system where a reversible fluidic pump is connected to an organoid 1 for inflation and deflation. The organoid 1 is subject to stretch based on changes in pressure delivered by the stimulation system and the pliability of the organoid 1.

Custom LabVIEW code automates a large portion of the process, including both hardware and software. Each organoid module 10 is discretely controlled via a single LabVIEW-powered computer (i.e., data processor 5). See FIG. 13 for exemplary software flow diagrams. Therefore, multiple organoids 1 and multiple organoid modules 10 are, or can be, monitored simultaneously under different conditions (FIG. 11). The LabVIEW code controls relevant hardware, such as data acquisition devices, multichannel digital output sources, valves, pumps and camera capture cards. Therefore, the code electronically controls multiple functions of the bioreactor platform or system, such as automatic drug perfusion and mixing, intraluminal pressure control, electrical stimulation, $CO_2$ and temperature control, and pressure transduction with synchronized image capture. The computer is outfitted with enough memory and storage space to continually capture data (e.g., sufficient for at least 24 hours of continuous data collection). Image acquisition is synchronized with other acquisition modalities of the bioreactor (e.g., intra-organoid pressure measurements) to enable clinically relevant endpoint measurements (e.g., pressure-volume loops). Several analytical functions within the LabVIEW code enhance and simplify user functionality of the bioreactor. Particle analysis of threshold digital images quantifies real-time volume of multiple discrete organoids 1, e.g., via a pyramidal mirror 13, which can be used to calculate contractile characteristics in real time for relevant organoids 1. These functions are, or can be, combined with the control of an electrical stimulator for automatic maximum capturing frequency analysis and related electrophysiological testing protocols. For example, for heart organoids 1, the LabVIEW code begins by sending a 0.5 Hz biphasic electrical stimulation pulse to the heart organoid 1 and monitors whether the organoid 1 captures the current frequency. The code automatically increases the rate of electrical stimulation until 1:1 capture is lost, where the heart organoid 1 beating frequency ceases to match the stimulation rate. Recording date, drug intervention times, electrical pacing regimens and additional information on each organoid 1 probed are saved as metadata for archiving and quality control purposes.

Example 10

Data Capture.

Figure 12:
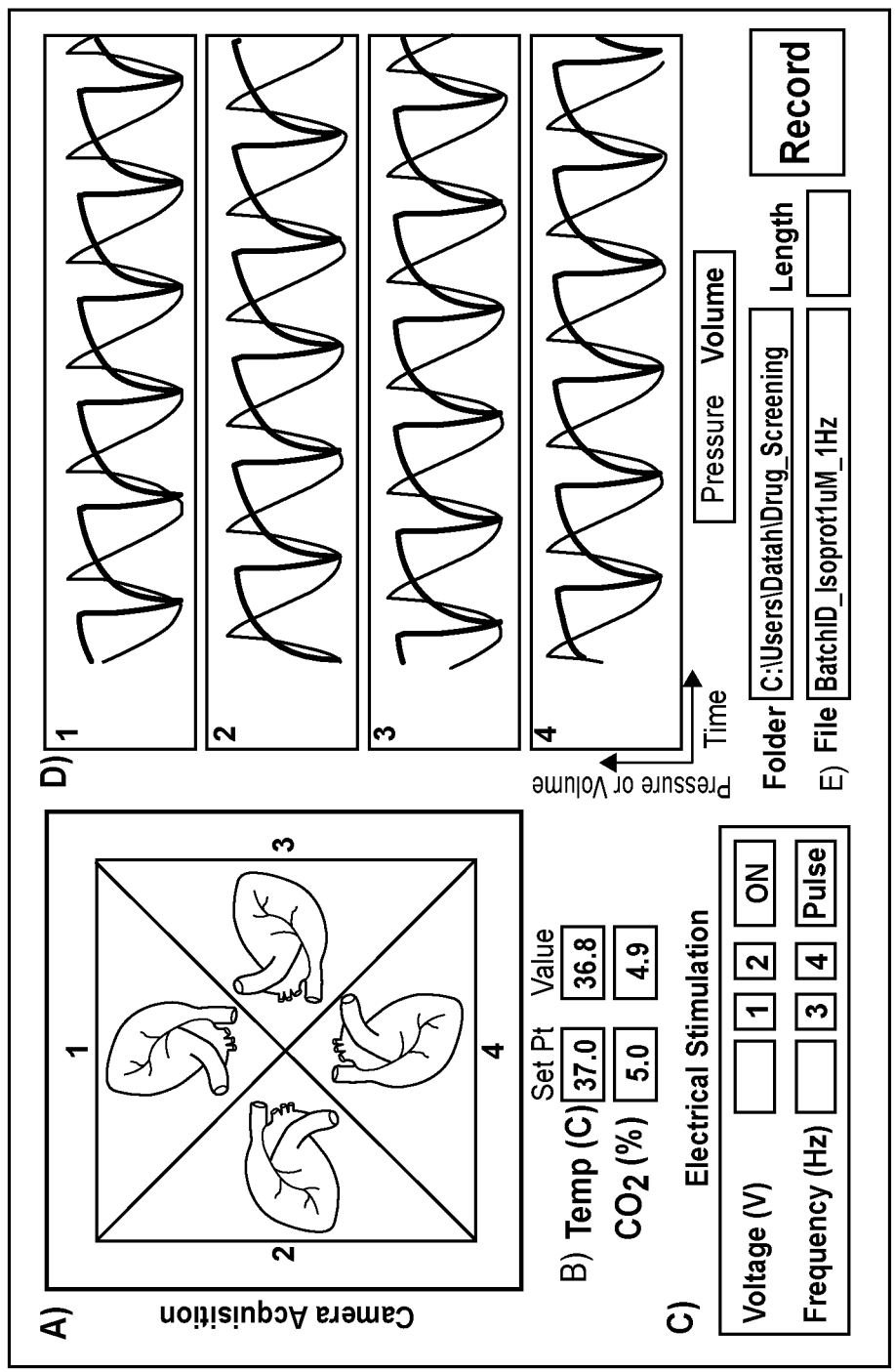
FIG. 12. Schematic of LabVIEW front panel for operating the bioreactor platform or system. A) Acquisition preview window of multiple organoids. B) Environmental control panel. C) Electrical stimulation parameters. The user has options to control the voltage power, alter the frequency, select which chambers to stimulate and decide to send continual stimulation or a single pulse. D) Real-time pressure, volume data of four distinct organoids. Pressure is represented as grey lines while organoid volume is represented as black lines. E) Recording parameters.
Figure 14A:
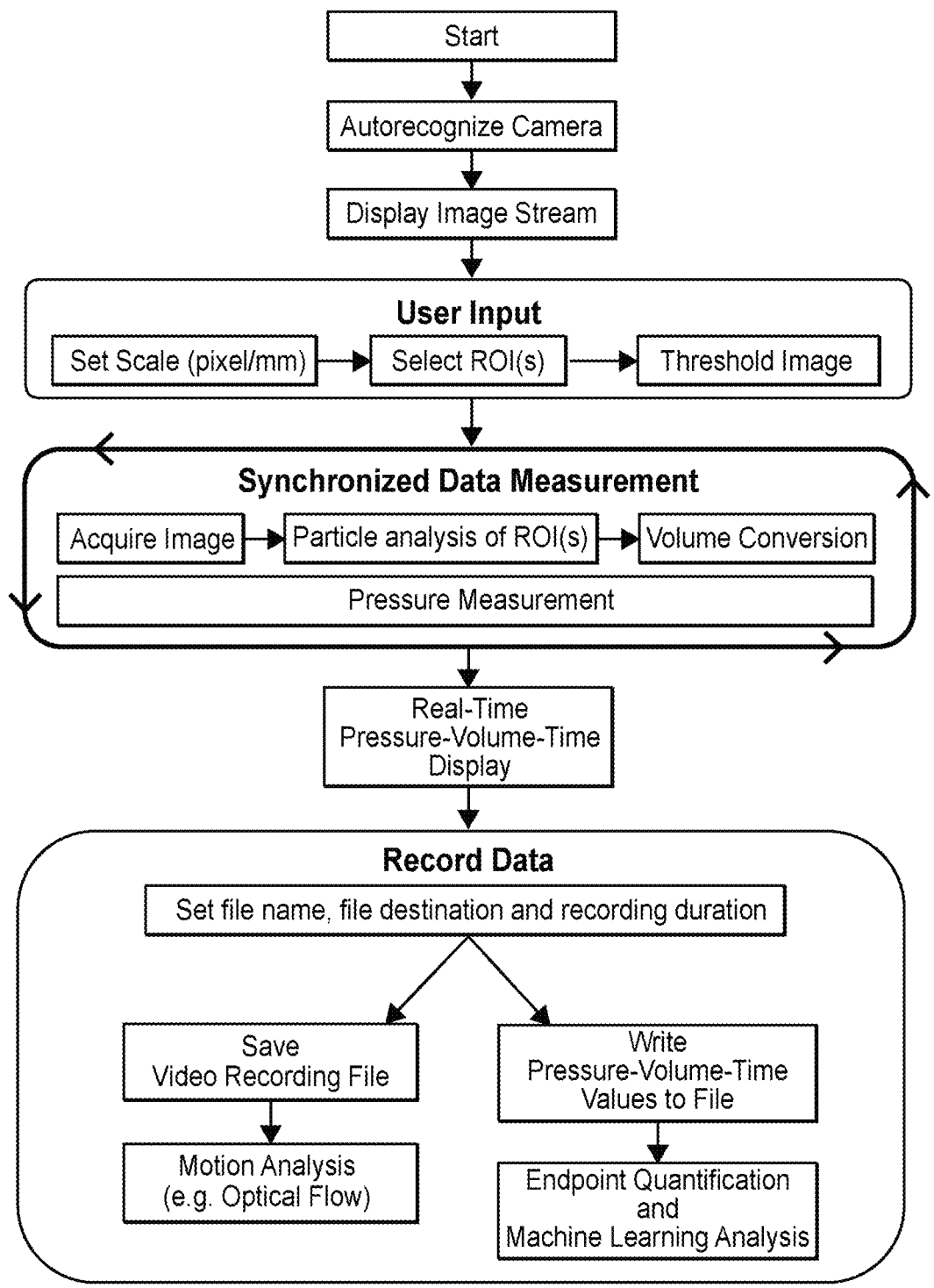
FIGS. 14A-14C. Flow diagrams of LabVIEW software used to monitor cells, tissues, and organoids in the system and apparatus disclosed herein. Flow diagrams schematically exemplify the software-based control of environmental variables, such as temperature and $CO_2$ level, and the software-based control of features of the system and apparatus, such as lens control, control of lighting, and control of electrical stimulation of cells, tissues and/or organoids contained in the system or apparatus.
Figure 14B:
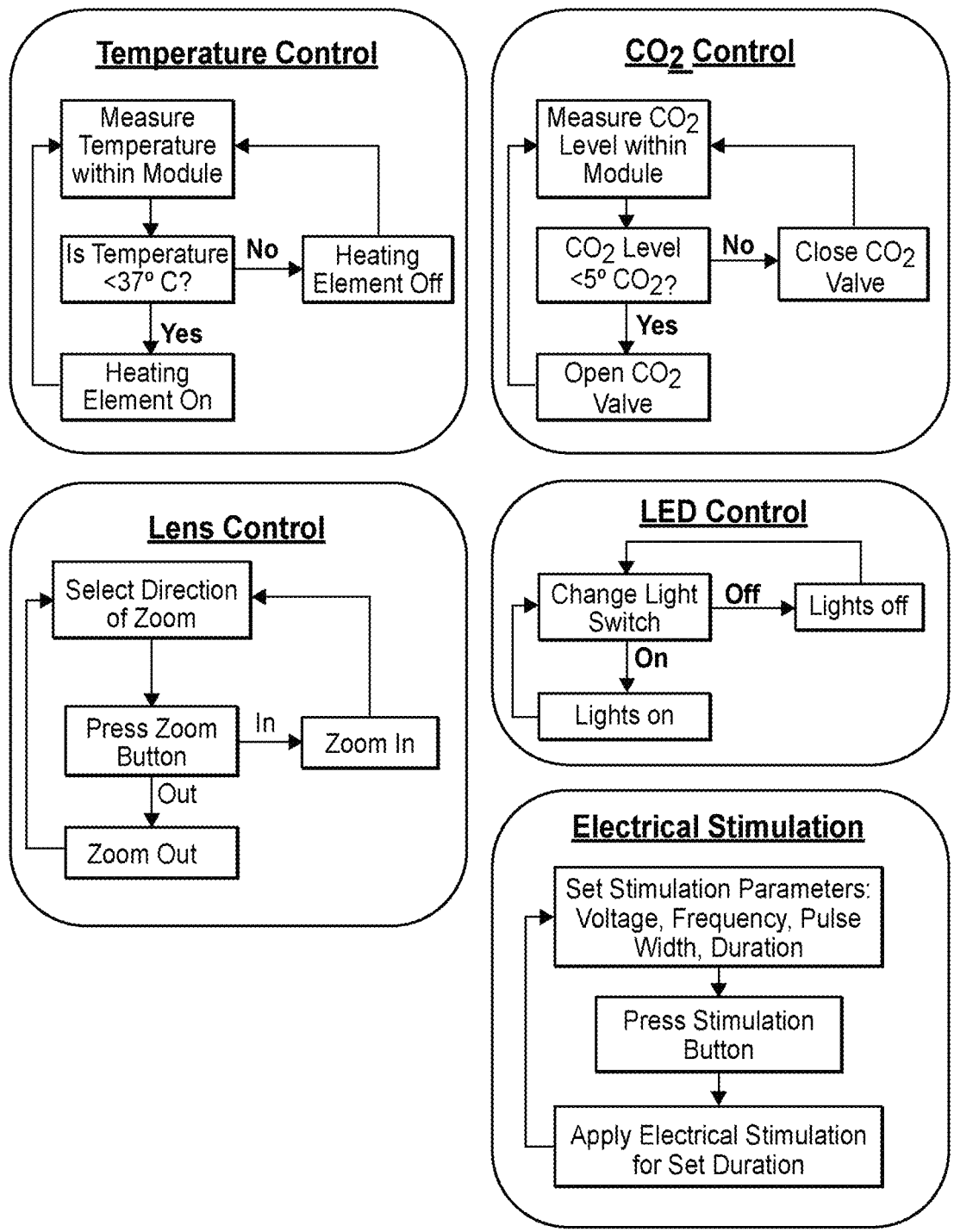
Figure 14C:
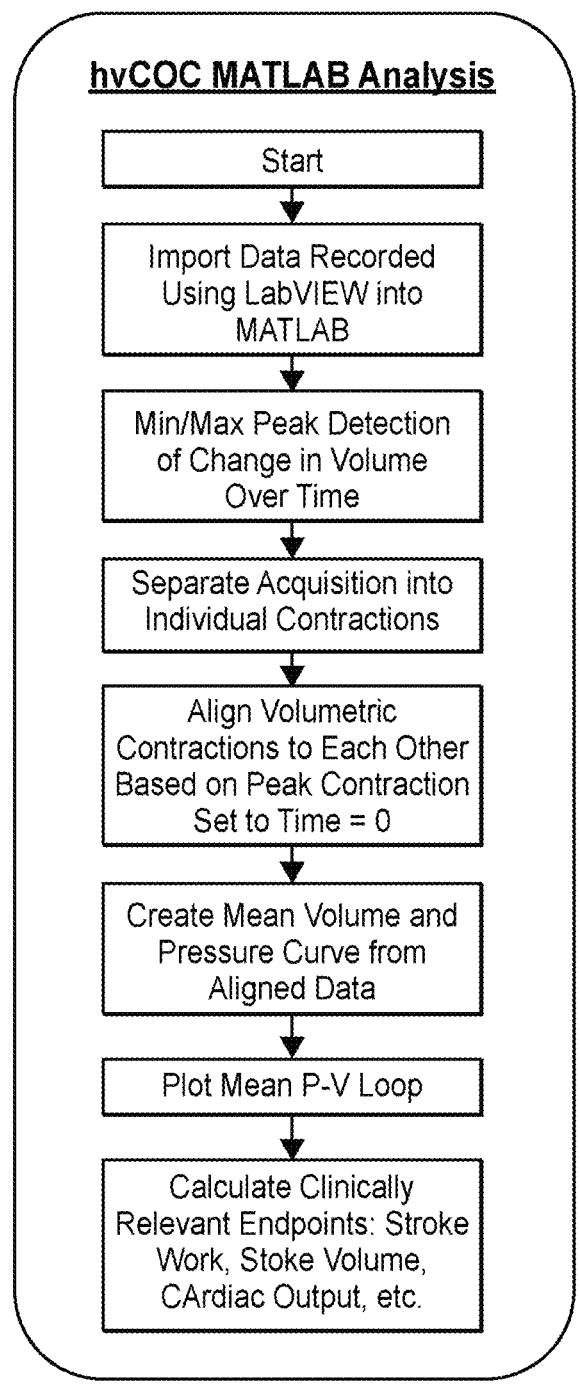

Pressure and volume data from the bioreactor are recorded simultaneously to generate pressure-volume curves in relevant contractile organoids. A high-speed digital camera (Allied Vision) acquires images up to 100 frames/second. Organoid volume is estimated by assuming an equivalent sphere with the same cross-sectional area. A single acquisition from, e.g., a heart organoid 1 typically contains multiple contractions. To characterize an organoid for its mean contraction characteristics, MATLAB code first separates the curve into discrete contractions. The data from each contraction are then aligned and averaged (FIG. 12A). The average pressure curve and average volume curve can then be plotted as the mean P-V loop (FIG. 12B).

Recorded high-speed brightfield videos are analyzed (e.g., optical flow) to characterize the motion pattern of the contractile organoids 1. Changes in contractile profile are analyzed to confirm therapeutic effects on organoid 1 contractile performance. To handle the large amount of multidimensional data acquisition, machine learning algorithms determine key parameters that correlate with a therapeutic response and, ultimately, classify unknown therapeutics into categories of interest. Additionally, machine learning can be executed concurrently with long-term data acquisition to identify rare abnormal events and minimize data storage. For example, long-term data acquisition can be broken into a continuous series of acquisitions. Completed acquisitions are sent to the buffer to be analyzed as further acquisitions continue. Machine learning (e.g., binary support vector machine) evaluates any abnormality in function from data within the buffer, such as a rare abnormal event. If an abnormality is detected, then the relevant data are permanently stored, while normal function data are discarded.

REFERENCES

1. Martelli A, Puccio H. Dysregulation of cellular iron metabolism in Friedreich ataxia: From primary iron-sulfur cluster deficit to mitochondrial iron accumulation. *Front Pharmacol.* 2014; 5:130.
2. Dixon S J, Stockwell B R. The role of iron and reactive oxygen species in cell death. *Nat Chem Biol.* 2014; 10:9-17.
3. Kipps A, Alexander M, Colan S D, Gauvreau K, Smoot L, Crawford L, Darras B T, Blume E D. The longitudinal course of cardiomyopathy in Friedreich's ataxia during childhood. *Pediatr Cardiol.* 2009; 30:306-310.
4. Casazza F, Morpurgo M. The varying evolution of Friedreich's ataxia cardiomyopathy. *Am J Cardiol.* 1996; 77:895-898.
5. Lynch D R, Regner S R, Schadt K A, Friedman L S, Lin K Y, St John Sutton M G. Management and therapy for cardiomyopathy in Friedreich's ataxia. *Expert Rev Cardiovasc Ther.* 2012; 10:767-777.
6. Weidemann F, Liu D, Hu K, Florescu C, Niemann M, Herrmann S, Kramer B, Klebe S, Doppler K, Uceyler N, Ritter C O, Ertl G, Stork S. The cardiomyopathy in Friedreich's ataxia—new biomarker for staging cardiac involvement. *Int J Cardiol.* 2015; 194:50-57.
7. Tsou A Y, Paulsen E K, Lagedrost S J, Perlman S L, Mathews K D, Wilmot G R, Ravina B, Koeppen A H, Lynch D R. Mortality in Friedreich ataxia. *J Neurol Sci.* 2011; 307:46-49.
8. Rajagopalan B, Francis J M, Cooke F, Korlipara L V, Blamire A M, Schapira A H, Madan J, Neubauer S, Cooper J M. Analysis of the factors influencing the cardiac phenotype in Friedreich's ataxia. *Mov Disord.* 2010; 25:846-852.
9. Payne R M, Pride P M, B abbey C M. Cardiomyopathy of Friedreich's ataxia: Use of mouse models to understand human disease and guide therapeutic development. Pediatr Cardiol. 2011; 32:366-378.
10. Dun A, Cossee M, Agid Y, Campuzano V, Mignard C, Penet C, Mandel J L, Brice A, Koenig M. Clinical and genetic abnormalities in patients with Friedreich's ataxia. *N Engl J Med.* 1996; 335:1169-1175.
11. Filla A, De Michele G, Cavalcanti F, Pianese L, Monticelli A, Campanella G, Cocozza S. The relationship between trinucleotide (gaa) repeat length and clinical features in Friedreich ataxia. *Am J Hum Genet.* 1996; 59:554-560.
12. Isnard R, Kalotka H, Durr A, Cossee M, Schmitt M, Pousset F, Thomas D, Brice A, Koenig M, Komajda M. Correlation between left ventricular hypertrophy and gaa trinucleotide repeat length in Friedreich's ataxia. *Circulation.* 1997; 95:2247-2249.
13. Puccio H, Simon D, Cossee M, Criqui-Filipe P, Tiziano F, Melki J, Hindelang C, Matyas R, Rustin P, Koenig M. Mouse models for Friedreich ataxia exhibit cardiomyopathy, sensory nerve defect and fe-s enzyme deficiency followed by intramitochondrial iron deposits. *Nat Genet.* 2001; 27:181-186.
14. Al-Mandawi S, Pinto R M, Varshney D, Lawrence L, Lowrie M B, Hughes S, Webster Z, Blake J, Cooper J M, King R, Pook M A. Gaa repeat expansion mutation mouse models of Friedreich ataxia exhibit oxidative stress leading to progressive neuronal and cardiac pathology. *Genomics.* 2006; 88:580-590.
15. Miranda C J, Santos M M, Ohshima K, Smith J, Li L, Bunting M, Cossee M, Koenig M, Sequeiros J, Kaplan J, Pandolfo M. Frataxin knockin mouse. *FEBS Lett.* 2002; 512:291-297.
16. Hick A, Wattenhofer-Donze M, Chintawar S, Tropel P, Simard J P, Vaucamps N, Gall D, Lambot L, Andre C, Reutenauer L, Rai M, Teletin M, Messaddeq N, Schiffmann S N, Viville S, Pearson C E, Pandolfo M, Puccio H. Neurons and cardiomyocytes derived from induced pluripotent stem cells as a model for mitochondrial defects in Friedreich's ataxia. *Dis Model Mech.* 2013; 6:608-621.
17. Lee Y K, Ho P W, Schick R, Lau Y M, Lai W H, Zhou T, Li Y, Ng K M, Ho S L, Esteban M A, Binah O, Tse H F, Siu C W. Modeling of Friedreich ataxia-related iron overloading cardiomyopathy using patient-specific-induced pluripotent stem cells. *Pflugers Arch.* 2014; 466: 1831-1844.
18. Lee Y K, Lau Y M, Ng K M, Lai W H, Ho S L, Tse H F, Siu C W, Ho P W. Efficient attenuation of Friedreich's ataxia (frda) cardiomyopathy by modulation of iron homeostasis-human induced pluripotent stem cell (hipsc) as a drug screening platform for frda. *Int J Cardiol.* 2016; 203:964-971.
19. Wang J, Chen A, Lieu D K, Karakikes I, Chen G, Keung W, Chan C W, Hajjar R J, Costa K D, Khine M, Li R A. Effect of engineered anisotropy on the susceptibility of human pluripotent stem cell-derived ventricular cardiomyocytes to arrhythmias. *Biomaterials.* 2013; 34:8878-8886.
20. Shum A M, Che H, Wong A O, Zhang C, Wu H, Chan C W, Costa K, Khine M, Kong C W, Li R A. A micropatterned human pluripotent stem cell-based ventricular cardiac anisotropic sheet for visualizing drug-induced arrhythmogenicity. *Adv Mater.* 2017; 29.
21. Chen A, Lieu D K, Freschauf L, Lew V, Sharma H, Wang J, Nguyen D, Karakikes I, Hajjar R J, Gopinathan A, Botvinick E, Fowles C C, Li R A, Khine M. Shrink-film configurable multiscale wrinkles for functional alignment of human embryonic stem cells and their cardiac derivatives. Adv. Mater. Weinheim 2011; 23:5785-5791.
22. Luna J, Ciriza J, Garcia-Ojeda M, Kong M, Herren A, Lieu D, Li R, Fowlkes C, Khine, M, McCloskey K. Multiscale Biomimetic Topography for the Alignment of Neonatal and Embryonic Stem Cell-Derived Heart Cells. Tissue Eng Part C Methods. 2011; 17:579-588.
23. Turnbull I C, Karakikes I, Serrao G W, Backeris P, Lee J-J J, Xie C, Senyei G, Gordon R E, Li R A, Akar F G, Hajjar R J, Hulot J-S, Costa K D. Advancing functional engineered cardiac tissues toward a preclinical model of human myocardium. FASEB J. 2014; 28:644-654.
24. Cashman T J, Josowitz R, Gelb B D, Li R A, Dubois N C, Costa K D. Construction of defined human engineered cardiac tissues to study mechanisms of cardiac cell therapy. *J Vis Exp.* 2016:e53447.
25. Weng Z, Kong C-W, Ren L, Karakikes I, Geng L, He J, Chow M Z, Mok C F, Keung W, Chow H, Leung A Y, Hajjar R J, Li R A, Chan C W. A simple, cost-effective but highly efficient system for deriving ventricular cardiomyocytes from human pluripotent stem cells. Stem Cells Dev. 2014; 23:1704-1716.
26. Goffart S, von Kleist-Retzow J C, Wiesner R J. Regulation of mitochondrial proliferation in the heart: Power-plant failure contributes to cardiac failure in hypertrophy. *Cardiovasc Res.* 2004; 64:198-207.
27. Ramirez R L, Becker A B, Mazurkiewicz J E, Feustel P J, Gelman B B, Koeppen A H. Pathology of intercalated discs in Friedreich cardiomyopathy. *J Am Coll Cardiol.* 2015; 66:1739-1740.
28. Edenharter O, Clement J, Schneuwly S, Navarro J A. Overexpression of *Drosophila* frataxin triggers cell death in an iron-dependent manner. *J Neurogenet.* 2017; 31:189-202.
29. Lopaschuk G D, Jaswal J S. Energy metabolic phenotype of the cardiomyocyte during development, differentiation, and postnatal maturation. *J Cardiovasc Pharmacol.* 2010; 56:130-140.
30. Keung, W., Ren, L., Sen Li, Wong, A. O., Chopra, A., Kong, C. W., Tomaselli G. F., Chen, C. S., Li, R. A. Non-cell autonomous cues for enhanced functionality of human embryonic stem cell-derived cardiomyocytes via maturation of sarcolemmal and mitochondrial K(ATP) channels. Sci Rep. 6, 34154 (2016).
31. Poon, E., Keung, W., Liang, Y., Ramalingam, R., Yan, B., Zhang, S., Chopra, A., Moore, J., Herren, A., Lieu, D. K., Wong, H. S., Weng, Z., Wong, O. T., Lam, Y. W., Tomaselli, G. F., Chen, C., Boheler, K. R. & Li, R. A. Proteomic Analysis of Human Pluripotent Stem Cell-Derived, Fetal, and Adult Ventricular Cardiomyocytes Reveals Pathways Crucial for Cardiac Metabolism and Maturation. Circ Cardiovasc Genet 8, 427-436 (2015).
32. Zhang, S., Poon, E., Xie, D., Boheler, K. R., Li, R. A., Wong, H. S. Consensus comparative analysis of human embryonic stem cell-derived cardiomyocytes. PLoS One. 10, e0125442 (2015).
33. Karakikes I., Stillitano F., Nonnenmacher M., Tzimas C., Sanoudou D., Termglinchan V., Kong C. W., Rushing S., Hansen J., Ceholski D., Kolokathis F., Kremastinos D., Katoulis A., Ren L., Cohen N., Gho J. M., Tsiapras D., Vink A., Wu J. C., Asselbergs F. W., Li R. A., Hulot J. S., Kranias E. G., Hajjar R. J. Correction of human phospholamban R14del mutation associated with cardiomyopathy using targeted nucleases and combination therapy. Nat Commun. 6, 6955 (2015).
34. Chen, G., Li, S., Karakikes, I., Ren, L., Chow, M. Z., Chopra, A., Keung, W., Yan, B., Chan, C. W., Costa, K. D., Kong, C. W., Hajjar, R. J., Chen, C. S., Li, R. A. Phospholamban as a crucial determinant of the inotropic response of human pluripotent stem cell-derived ventricular cardiomyocytes and engineered 3-dimensional tissue constructs. Circ Arrthyhm Electrophysiol. 8, 193-201 (2015).
35. Weng, Z., Kong, C.-W., Ren, L., Karakikes, I., Geng, L., He, J., Chow, M. Z. Y., Mok, C. F., Chan, H. Y. S., Webb, S. E., Keung, W., Chow, H., Miller, A. L., Leung, A. Y. H., Hajjar, R. J., Li, R. A. & Chan, C. W. A Simple, Cost-Effective but Highly Efficient System for Deriving Ventricular Cardiomyocytes from Human Pluripotent Stem Cells. Stem Cells Dev. 23, 1704-1716 (2014).
36. Karakikes, I., Senyel, G. D., Hansen, J., Kong, C.-W., Azeloglu, E. U., Stillitano, F., Lieu, D. K., Wang, J., Ren, L., Hulot, J.-S., Iyengar, R., Li, R. A. & Hajjar, R. j. Small Molecule-Mediated Directed Differentiation of Human Embryonic Stem Cells Toward Ventricular Cardiomyocytes. Stem Cells Transl. Med. 3, 18-31 (2014).
37. Li, S., Cheng, H., Tomaselli, G. F., Li, R. A. Mechanistic basis of excitation-contraction coupling in human pluripotent stem cell-derived ventricular cardiomyocytes revealed by Ca2+ spark characteristics: direct evidence of functional Ca2+-induced Ca2+ release. Heart Rhythm. 11, 133-140 (2014).
38. Poon, E., Yan, B., Zhang, S., Rushing, S., Keung, W., Ren, L., Lieu, D. K., Geng, L., Kong, C. W., Wang, J., Wong H. S., Boheler, K. R., Li, R. A. Transcriptome-guided functional analyses reveal novel biological properties and regulatory hierarchy of human embryonic stem cell-derived ventricular cardiomyocytes crucial for maturation. PLoS One. 8, e77784 (2013).
39. Chow, M. Z., Geng, L., Kong, C. W., Keung, W., Fung, J. C., Boheler, K. R., Li, R. A. Epigenetic regulation of the electrophysiological phenotype of human embryonic stem cell-derived ventricular cardiomyocytes: insights for driven maturation and hypertrophic growth. Stem Cells Dev. 22, 2678-2690 (2013).
40. Lieu, D. K., Fu, J. D., Chiamvimonvat, N., Tung, K. C., McNerney, G. P., Huser, T., Keller, G., Kong, C. W., Li, R. A. Mechanism-based facilitated maturation of human pluripotent stem cell-derived cardiomyocytes. Circ Arrhythm Electrophysiol. 6, 191-201 (2013).
41. Fu, J. D., Rushing, S. N., Lieu, D. K., Chan, C. W., Kong, C. W., Geng, L., Wilson, K. D., Chiamvimonvat, N., Boheler, K. R., Wu, J. C., Keller, G., Hajjar, R. J., Li, R. A. Distinct roles of microRNA-1 and -499 in ventricular specification and functional maturation of human embryonic stem cell-derived cardiomyocytes. PLoS One. 6, e27417 (2011).
42. Wilson, K. D., Hu, S., Venkatasubrahmanyam, S., Fu, J. D., Sun, N., Abilez, O. J., Baugh, J. J., Jia, F., Ghosh, Z., Li, R. A., Butte, A. J., Wu, J. C. Dynamic microRNA expression programs during cardiac differentiation of human embryonic stem cells: role for miR-499. Circ Cardiovasc Genet. 3, 426-435 (2010).
43. Fu, J. D., Jiang, P., Rushing, S., Liu, J., Chiamvimonvat, N., Li, R. A. Na+/Ca2+ exchanger is a determinant of excitation-contraction coupling in human embryonic stem cell-derived ventricular cardiomyocytes. Stem Cells Dev. 19, 773-782 (2010).
44. Liu, J., Lieu, D. K., Siu, C. W., Fu, J. D., Tse, H. F., Li, R. A. Facilitated maturation of Ca2+ handling properties of human embryonic stem cell-derived cardiomyocytes by calsequestrin expression. Am J Physiol Cell Physiol. 297, C152-159 (2009).
45. Lieu, D. K., Liu, J., Siu, C. W., McNerney, G. P., Tse, H. F., Abu-Khalil, A., Huser, T., Li, R. A. Absence of transverse tubules contributes to non-uniform Ca(2+) wavefronts in mouse and human embryonic stem cell-derived cardiomyocytes. Stem Cells Dev. 18, 1493-1500 (2009).
46. Chan, J. W., Lieu, D. K., Huser, T., Li, R. A. Label-free separation of human embryonic stem cells and their cardiac derivatives using Raman spectroscopy. Anal Cham. 81, 1324-1331 (2009).
47. Liu J., Fu J. D., Siu C. W., Li R. A. Functional sarcoplasmic reticulum for calcium handling of human embryonic stem cell-derived cardiomyocytes: insights for driven maturation. Stem Cells. 12, 3038-44 (2007).
48. Wang K., Xue T., Tsang S. Y., Van Huizen R., Wong C. W., Lai K. W., Ye Z., Cheng L., Au K. W., Zhang J., Li G. R., Lau C. P., Tse H. F., Li R. A. Electrophysiological properties of pluripotent human and mouse embryonic stem cells. Stem Cells. 10, 1526-34 (2005)

49. Li, R. A., et al., *Bioengineering an electro-mechanically functional miniature ventricular heart chamber from human pluripotent stem cells*. Biomaterials, 2018. 163: p. 116-127.

Each of the references cited herein is hereby incorporated by reference in its entirety or in relevant part, as would be apparent from the context of the citation.

It is to be understood that while the claimed subject matter has been described in conjunction with the detailed description thereof, the foregoing description is intended to illustrate and not limit the scope of that claimed subject matter, which is defined by the scope of the appended claims. Other aspects, advantages, and modifications are within the scope of the following claims.

What is claimed is:

1. A system for screening a compound for a cardiac effect on cardiomyocytes of a diseased organism or engineered cardiomyocytes comprising:
    (a) a screening apparatus comprising:
        (i) a biocompatible gel comprising a plurality of cardiomyocytes of a diseased organism or a plurality of engineered cardiomyocytes;
        (ii) a biocompatible support apparatus for suspending the biocompatible gel, wherein the biocompatible gel and biocompatible support apparatus form a cardiac tissue strip comprising cardiomyocytes of a diseased organism or engineered cardiomyocytes;
        (iii) a detection device for detecting movement of the biocompatible gel; and
        (iv) an electrical power source for applying an electrical pacing stimulus to the biocompatible gel; and
    (b) a second-stage screening apparatus comprising:
        (i) at least one organoid module comprising at least one organoid cartridge, wherein the organoid cartridge comprises a media inlet, a media outlet, and at least one wall compatible with an external detection device, wherein each organoid cartridge comprises a cardiomyocyte or a plurality of cardiomyocytes of a diseased organism or an engineered cardiomyocyte or a plurality of engineered cardiomyocytes, and wherein at least one organoid cartridge comprises cardiomyocytes of a diseased organism or engineered cardiomyocytes; and
        (ii) a detection device for observing the monitored biological development of the cardiomyocytes of the diseased organism or the engineered cardiomyocytes in each organoid cartridge.

2. The system of claim 1, wherein the second-stage screening apparatus further comprises a mirror arrangement for simultaneous monitoring of any biological development of the cardiomyocytes of a diseased organism or engineered cardiomyocytes in each organoid cartridge.

3. The system of claim 1, wherein the cardiomyocytes are human cardiomyocytes.

4. The system of claim 1, wherein the cardiomyocytes are engineered cardiomyocytes or are derived from a patient having Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers).

5. The system of claim 4, wherein the cardiomyocytes are engineered to have low FXN expression or are derived from a patient with Friedreich's ataxia (FRDA).

6. The system of claim 1, wherein the biocompatible gel comprises matrigel or a combination of matrigel and collagen.

7. The system of claim 1, wherein the support apparatus is at least two vertical support members made of polydimethylsiloxane.

8. The system of claim 1, wherein the second-stage screening apparatus further comprises a temperature control element, a light source, a module access port, or any combination thereof.

9. The system of claim 1, wherein the second-stage screening apparatus further comprises a data processor in electronic communication with the detection device, a temperature control element, a light source, a module access port or any combination thereof.

10. The system of claim 1, wherein the detection device is a digital camera, at least one pressure transducer, or a combination of a digital camera and at least one pressure transducer.

11. The system of claim 1 comprising a plurality of organoid modules.

12. The system of claim 1 further comprising an interconnected fluid exchange network, wherein the network comprises a plurality of fluid lines, a plurality of valves, at least one pump, and at least one fluid tank.

13. The system of claim 12 further comprising a port for introduction of a compound.

14. The system of claim 12 wherein the fluid is media.

15. The system according to claim 1 further comprising a gas pressure controller.

16. The system according to claim 1 further comprising a drug perfusion apparatus for delivery of a compound to the cardiomyocytes.

17. The system of claim 1, wherein the detection device is a high-speed camera.

18. The system of claim 1, wherein the mirror arrangement of the second-stage screening apparatus comprises at least one pyramidal mirror.

19. The system of claim 1, wherein the screening apparatus further comprises an electrode in adjustable relation to the cardiomyocytes in at least one organoid cartridge.

20. The system of claim 12, wherein the interconnected fluid exchange network comprises fluid communication between at least two organoid cartridges.

21. A system for screening a compound for a cardiac effect on cardiomyocytes of a diseased organism or engineered cardiomyocytes comprising:
    (a) a screening device comprising:
        (i) an anisotropic layer of cardiac cells on a microfabricated substrate;
        (ii) an electrical power source for stimulating the anisotropic layer of cells at one or more points; and
        (iii) a detection device for detecting an electrical signal propagation in the anisotropic layer of cells; and
    (b) a second-stage screening apparatus comprising:
        (i) at least one organoid module comprising at least one organoid cartridge, wherein the organoid cartridge comprises a media inlet, a media outlet, and at least one wall compatible with an external detection device, wherein each organoid cartridge comprises a cardiomyocyte or a plurality of cardiomyocytes of a diseased organism or an engineered cardiomyocyte or a plurality of engineered cardiomyocytes, and wherein at least one organoid cartridge comprises cardiomyocytes of a diseased organism or engineered cardiomyocytes; and (ii) a detection device for observing the monitored biological development of the cardiomyocytes of the diseased organism or the engineered cardiomyocytes in each organoid cartridge.

22. The system of claim 21, wherein the cardiomyocytes are engineered cardiomyocytes or are derived from a patient having Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), or MERRF (myoclonic epilepsy with ragged red fibers).

23. The system of claim 21, wherein the cardiomyocytes are engineered to have low frataxin (FXN) expression or are derived from a patient with Friedreich's ataxia (FRDA).

24. The system of claim 21, wherein the microfabricated substrate comprises grooves oriented along a single axis of the substrate.

25. The system of claim 21, wherein the electrical power source is at least one electrode or at least one electrified portion of the substrate.

* * * * *

UNITED STATES PATENT AND TRADEMARK OFFICE
CERTIFICATE OF CORRECTION

| | | |
|---|---|---|
| PATENT NO. | : 12,265,078 B2 | Page 1 of 1 |
| APPLICATION NO. | : 17/041912 | |
| DATED | : April 1, 2025 | |
| INVENTOR(S) | : Ronald A. Li et al. | |

It is certified that error appears in the above-identified patent and that said Letters Patent is hereby corrected as shown below:

On the Title Page

At Item (57), Line 10, "(hvCOC) (20)," should be -- (hvCOC) (1), --.

Signed and Sealed this
Sixteenth Day of December, 2025

John A. Squires
*Director of the United States Patent and Trademark Office*